(12) United States Patent
Wang et al.

(10) Patent No.: US 8,110,359 B2
(45) Date of Patent: Feb. 7, 2012

(54) **PCR METHOD FOR IDENTIFIYING A SEROTYPE OF *KLEBSIELLA PNEUMONIAE* BY USING CPS REGION PRIMERS AND APPLICATION THEREOF**

(75) Inventors: Jin-Town Wang, Taipei (TW); Yi-Jiun Pan, Taipei (TW); Han-Chi Fang, Taipei (TW); Hui-Ching Yang, Taipei (TW); Tzu-Lung Lin, Taipei (TW); Pei-Fang Hsieh, Taipei (TW); Feng-Chiao Tsai, Taipei (TW); Yoav Keynan, Taipei (TW)

(73) Assignee: National Taiwan University, Taipei (TW)

( * ) Notice: Subject to any disclaimer, the term of this patent is extended or adjusted under 35 U.S.C. 154(b) by 345 days.

(21) Appl. No.: 12/424,062

(22) Filed: Apr. 15, 2009

(65) Prior Publication Data

US 2010/0136534 A1 Jun. 3, 2010

(30) Foreign Application Priority Data

Nov. 28, 2008 (TW) ................................ 97146314 A

(51) Int. Cl.
*C12Q 1/68* (2006.01)
*C12P 19/34* (2006.01)
*C07H 21/04* (2006.01)

(52) U.S. Cl. .................... 435/6.12; 435/91.2; 536/24.33

(58) Field of Classification Search ................. 435/6.12, 435/91.2; 536/24.33
See application file for complete search history.

(56) References Cited

U.S. PATENT DOCUMENTS

2011/0065111 A1 * 3/2011 Sampath et al. ................. 435/6

OTHER PUBLICATIONS

Yu et al., Journal of Infectious Diseases 195, 1235-1236 (2007).*
Pan, et al.,Capsular Polysaccharide Synthesis Regions in *Klebsiella pneumoniae* Serotype K57 and a New Capsular Serotype, Journal, Jul. 2008, Journal of Clinical Microbiology, pp. 2231-2240, American Society for Microbiology.

* cited by examiner

*Primary Examiner* — Kenneth R. Horlick
(74) *Attorney, Agent, or Firm* — WPAT, P.C.; Anthony King

(57) ABSTRACT

The present invention relates to a method of identifying a serotype of *Klebsiella pneumoniae*, in particular to a method using specific polymerase chain reaction (PCR) primer sets designed according to a fragment of a capsular polysaccharide synthesis (cps) region to identify a K57 or a NTUH-N1 serotype and its application. NTUH-N1 is a novel serotype which differs from the previously reported 77 serotypes. This PCR-based cps genotyping method not only solves the problems of insufficient specificity and sensitivity caused by conventional immune method, but can be applied in clinical diagnosis with the advantages of rapidity and low cost. In addition, the rate of unidentifiable strains can also be reduced by this method.

3 Claims, 7 Drawing Sheets

A.

B.

A.

B.

SEQUENCE LISTING

<160> NUMBER OF SEQ ID NOS: 45

<210> SEQ ID NO 1
<211> LENGTH: 24
<212> TYPE: DNA
<213> ORGANISM: Artificial Sequence
<220> FEATURE:
<223> OTHER INFORMATION: cps region PCR primer

<400> SEQUENCE: 1
cgacctggcc tggctttccg atcg                                          24

<210> SEQ ID NO 2
<211> LENGTH: 25
<212> TYPE: DNA
<213> ORGANISM: Artificial Sequence
<220> FEATURE:
<223> OTHER INFORMATION: cps region PCR primer

<400> SEQUENCE: 2
gccgggttag tggtaaatga caacg                                         25

<210> SEQ ID NO 3
<211> LENGTH: 22
<212> TYPE: DNA
<213> ORGANISM: Artificial Sequence
<220> FEATURE:
<223> OTHER INFORMATION: cps region PCR primer

<400> SEQUENCE: 3
tcatccatct gagcctgtcg ac                                            22

<210> SEQ ID NO 4
<211> LENGTH: 22
<212> TYPE: DNA
<213> ORGANISM: Artificial Sequence
<220> FEATURE:
<223> OTHER INFORMATION: cps region PCR primer

<400> SEQUENCE: 4
gaagttctgg aaccagtggc tc                                            22

```
<210> SEQ ID NO 5
<211> LENGTH: 20
<212> TYPE: DNA
<213> ORGANISM: Artificial Sequence
<220> FEATURE:
<223> OTHER INFORMATION: cps region PCR primer

<400> SEQUENCE: 5
tcataacgga ggataccagc                                              20

<210> SEQ ID NO 6
<211> LENGTH: 24
<212> TYPE: DNA
<213> ORGANISM: Artificial Sequence
<220> FEATURE:
<223> OTHER INFORMATION: cps region PCR primer

<400> SEQUENCE: 6
caagcaacag atcgggttg tcgg                                          24

<210> SEQ ID NO 7
<211> LENGTH: 20
<212> TYPE: DNA
<213> ORGANISM: Artificial Sequence
<220> FEATURE:
<223> OTHER INFORMATION: cps region PCR primer

<400> SEQUENCE: 7
cgagggattc aacaaactct                                              20

<210> SEQ ID NO 8
<211> LENGTH: 22
<212> TYPE: DNA
<213> ORGANISM: Artificial Sequence
<220> FEATURE:
<223> OTHER INFORMATION: cps region PCR primer

<400> SEQUENCE: 8
gatggtgtcc tggaagaagg tg                                           22

<210> SEQ ID NO 9
<211> LENGTH: 20
<212> TYPE: DNA
<213> ORGANISM: Artificial Sequence
<220> FEATURE:
<223> OTHER INFORMATION: cps region PCR primer

<400> SEQUENCE: 9
taccgtctcc gttttcaacc                                              20

<210> SEQ ID NO 10
<211> LENGTH: 20
<212> TYPE: DNA
<213> ORGANISM: Artificial Sequence
<220> FEATURE:
<223> OTHER INFORMATION: cps region PCR primer

<400> SEQUENCE: 10
gtaaggaacc agcttcttgc                                              20

<210> SEQ ID NO 11
<211> LENGTH: 25
<212> TYPE: DNA
<213> ORGANISM: Artificial Sequence
<220> FEATURE:
<223> OTHER INFORMATION: cps region sequencing primer
```

```
<400> SEQUENCE: 11
acctacaaca aagctctcat caacc                                          25

<210> SEQ ID NO 12
<211> LENGTH: 25
<212> TYPE: DNA
<213> ORGANISM: Artificial Sequence
<220> FEATURE:
<223> OTHER INFORMATION: cps region sequencing primer

<400> SEQUENCE: 12
gcaatgtaac atcagagatt ttgag                                          25

<210> SEQ ID NO 13
<211> LENGTH: 20
<212> TYPE: DNA
<213> ORGANISM: Artificial Sequence
<220> FEATURE:
<223> OTHER INFORMATION: A1142 cps 5'PCR primer

<400> SEQUENCE: 13
gagccgctga ataacctgaa                                                20

<210> SEQ ID NO 14
<211> LENGTH: 20
<212> TYPE: DNA
<213> ORGANISM: Artificial Sequence
<220> FEATURE:
<223> OTHER INFORMATION: A1142 cps 5'PCR primer

<400> SEQUENCE: 14
gctcagaaga ataggacggt                                                20

<210> SEQ ID NO 15
<211> LENGTH: 19
<212> TYPE: DNA
<213> ORGANISM: Artificial Sequence
<220> FEATURE:
<223> OTHER INFORMATION: A1142 cps 3'PCR primer

<400> SEQUENCE: 15
gtgccatggt gcttggtgg                                                 19

<210> SEQ ID NO 16
<211> LENGTH: 20
<212> TYPE: DNA
<213> ORGANISM: Artificial Sequence
<220> FEATURE:
<223> OTHER INFORMATION: A1142 cps 3'PCR primer

<400> SEQUENCE: 16
gatgaccatc ggttcatgga                                                20

<210> SEQ ID NO 17
<211> LENGTH: 20
<212> TYPE: DNA
<213> ORGANISM: Artificial Sequence
<220> FEATURE:
<223> OTHER INFORMATION: A1517 cps 5'PCR primer

<400> SEQUENCE: 17
ggcgcgacgt cataatactg                                                20

<210> SEQ ID NO 18
<211> LENGTH: 20
```

```
-continued

<212> TYPE: DNA
<213> ORGANISM: Artificial Sequence
<220> FEATURE:
<223> OTHER INFORMATION: A1517 cps 5'PCR primer

<400> SEQUENCE: 18
gagaaggtaa agcggccacc                                               20

<210> SEQ ID NO 19
<211> LENGTH: 20
<212> TYPE: DNA
<213> ORGANISM: Artificial Sequence
<220> FEATURE:
<223> OTHER INFORMATION: A1517 cps 3'PCR primer

<400> SEQUENCE: 19
gaccgaagaa gtgattgccg                                               20

<210> SEQ ID NO 20
<211> LENGTH: 20
<212> TYPE: DNA
<213> ORGANISM: Artificial Sequence
<220> FEATURE:
<223> OTHER INFORMATION: A1517 cps 3'PCR primer

<400> SEQUENCE: 20
cgcgttcggg ttgatctttg                                               20

<210> SEQ ID NO 21
<211> LENGTH: 17
<212> TYPE: DNA
<213> ORGANISM: Artificial Sequence
<220> FEATURE:
<223> OTHER INFORMATION: cps-PCR genotyping mutant construct primer

<400> SEQUENCE: 21
atggcgtgcc tcgtgag                                                  17

<210> SEQ ID NO 22
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 22
gttatagcac caattacagc                                               20

<210> SEQ ID NO 23
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 23
gtcatctgca caggatgaca                                               20

<210> SEQ ID NO 24
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 24
cttcgctacc gtgtagcatt                                               20
```

```
<210> SEQ ID NO 25
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 25
gcaagacaag aatgggatgc                                              20

<210> SEQ ID NO 26
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 26
gacatactac cgcatttgcg                                              20

<210> SEQ ID NO 27
<211> LENGTH: 19
<212> TYPE: DNA
<213> ORGANISM: Artificial Sequence
<220> FEATURE:
<223> OTHER INFORMATION: cps-PCR genotyping primer

<400> SEQUENCE: 27
cagtgagtta gagttaccg                                               19

<210> SEQ ID NO 28
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 28
gctacacata agtccgagtg                                              20

<210> SEQ ID NO 29
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 29
gcaagtgagc aaagtaatgc                                              20

<210> SEQ ID NO 30
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 30
aggctcatct ctcccttcag                                              20

<210> SEQ ID NO 31
<211> LENGTH: 18
<212> TYPE: DNA
<213> ORGANISM: Artificial Sequence
<220> FEATURE:
<223> OTHER INFORMATION: cps-PCR genotyping primer
```

<400> SEQUENCE: 31
gggacactct tatttcac                                                 18

<210> SEQ ID NO 32
<211> LENGTH: 18
<212> TYPE: DNA
<213> ORGANISM: Artificial Sequence
<220> FEATURE:
<223> OTHER INFORMATION: cps-PCR genotyping primer

<400> SEQUENCE: 32
ctgggatgct gaccatgg                                                 18

<210> SEQ ID NO 33
<211> LENGTH: 20
<212> TYPE: DNA
<213> ORGANISM: Artificial Sequence
<220> FEATURE:
<223> OTHER INFORMATION: cps-PCR genotyping primer

<400> SEQUENCE: 33
cgtagactca tccactcttt                                               20

<210> SEQ ID NO 34
<211> LENGTH: 19
<212> TYPE: DNA
<213> ORGANISM: Artificial Sequence
<220> FEATURE:
<223> OTHER INFORMATION: cps-PCR genotyping primer

<400> SEQUENCE: 34
gagggtattg atttaggtc                                                19

<210> SEQ ID NO 35
<211> LENGTH: 19
<212> TYPE: DNA
<213> ORGANISM: Artificial Sequence
<220> FEATURE:
<223> OTHER INFORMATION: cps-PCR genotyping primer

<400> SEQUENCE: 35
ctacagaaac catcccgcc                                                19

<210> SEQ ID NO 36
<211> LENGTH: 18
<212> TYPE: DNA
<213> ORGANISM: Artificial Sequence
<220> FEATURE:
<223> OTHER INFORMATION: Mutant construct primer

<400> SEQUENCE: 36
ctattgagca gtctgtag                                                 18

<210> SEQ ID NO 37
<211> LENGTH: 22
<212> TYPE: DNA
<213> ORGANISM: Artificial Sequence
<220> FEATURE:
<223> OTHER INFORMATION: Mutant construct primer

<400> SEQUENCE: 37
ttttaagata atccttatcg ag                                            22

<210> SEQ ID NO 38
<211> LENGTH: 18

```
<212> TYPE: DNA
<213> ORGANISM: Artificial Sequence
<220> FEATURE:
<223> OTHER INFORMATION: Mutant construct primer

<400> SEQUENCE: 38
tcttatttgt gaggtgtg                                                   18

<210> SEQ ID NO 39
<211> LENGTH: 17
<212> TYPE: DNA
<213> ORGANISM: Artificial Sequence
<220> FEATURE:
<223> OTHER INFORMATION: trans-complementation primer

<400> SEQUENCE: 39
agactttctc gataagg                                                    17

<210> SEQ ID NO 40
<211> LENGTH: 18
<212> TYPE: DNA
<213> ORGANISM: Artificial Sequence
<220> FEATURE:
<223> OTHER INFORMATION: trans-complementation primer

<400> SEQUENCE: 40
tgcttctctc atacacac                                                   18

<210> SEQ ID NO 41
<211> LENGTH: 31
<212> TYPE: DNA
<213> ORGANISM: Artificial Sequence
<220> FEATURE:
<223> OTHER INFORMATION: cps region PCR primer

<400> SEQUENCE: 41
gctggtagct gttaagccag gggcggtagc g                                    31

<210> SEQ ID NO 42
<211> LENGTH: 35
<212> TYPE: DNA
<213> ORGANISM: Artificial Sequence
<220> FEATURE:
<223> OTHER INFORMATION: cps region PCR primer

<400> SEQUENCE: 42
tattcatcag aagcagcacg cagctgggag aagcc                                35

<210> SEQ ID NO 43
<211> LENGTH: 33
<212> TYPE: DNA
<213> ORGANISM: Artificial Sequence
<220> FEATURE:
<223> OTHER INFORMATION: cps region PCR primer

<400> SEQUENCE: 43
gcgctctggc tggtccattt accggtccct ttg                                  33

<210> SEQ ID NO 44
<211> LENGTH: 20795
<212> TYPE: DNA
<213> ORGANISM: Klebsiella pneumoniae

<400> SEQUENCE: 44
atggcgaact tgaaagcggt tattccggtc gcaggactag gcatgcatat gctgccggcc     60
acaaaggcaa ttccaaagga gatgctgccg atcgttgata agccaatgat tcagtacatc    120
```

-continued

```
gttgacgaaa tcgtcgccgc cgggatcaaa gagattgttc tggtgacgca ctcctcgaag      180
aacgcggtgg aaaaccactt cgatacctcc tacgagctgg aagccctgct ggaacagcgc      240
gtgaagcgcc agctgctggc ggaagtgcag gccatttgcc cgccgggcgt gaccatcatg      300
aacgtgcgtc aggcgcagcc gctgggcctg ggccactcca tcctctgcgc ccgcccggta      360
gtcggcgaca acccgtttgt ggtggtcctg ccggatatca tccttgacgg cggcaccgct      420
gacccgctgc gctataacct cgccgctatg atcgcccgct ttaacgagac cggccgcagc      480
caggtgctgg cgaaacgcat gccgggcgat ctctccgaat actccgtcat ccagaccaaa      540
gagccaatgg tggctgaagg ccaggtggcg cgtatcgttg agtttattga aaaaccggac      600
gaaccgcaga ccctggactc cgacctgatg gcggtggggc gctacgtgct gtcggcggat      660
atctgggccg aactggaacg taccgagccg ggcgcatggg gccgtatcca gctgaccgac      720
gccattgccg aactggcgaa gaagcagtcc gtcgacgcga tgctgatgac cggcgaaagc      780
tacgactgcg ggaagaaaat gggctacatg caggccttcg tcacctacgg gatgcgtaac      840
ctgaaagaag cgccaaatt ccgcgaaagt attaaaaaaa tgctggcctg attgctagcg      900
tagtacgggg ggcagggcgt gaatattcgt cctgccgctc ataacgttat gcagaaatta      960
ttcataacgc gaatgttata acgattgtaa agaaacgtat ggcttcggag acttctggta     1020
gtttgtctct ggcctctgtg gtgcaatggt cggagtagcg gcaataatgc tttatgaata     1080
gtcacttagt gcgacaattc ctaaagcgca gggaaagcgg tcaacgtcag ccaaaaataa     1140
aacttgactg cgatcatgtt tccgctttaa acatctcact tgcatgcata aaaatgtgaa     1200
atgaattggc atgcgagctg gtacagacat tacggataat ccctgagcac ggcagtggac     1260
atcatcgaag gatcacaggt atatgaactg gcaactcatc tcattttttg gcgatagcac     1320
tgttttgctg cccagcgcag cggcgctgtt tattgtcctg atgctgcgta aacgtcgcg      1380 gttgctggcg tggcagtgga gtttgctgtt cggcatcacc ggcgctatcg tctgcgcctc     1440
caaactggcc tttatgggct ggggtctggg tattcgtgaa ctggattaca ccggcttcag     1500
cggccactcc gcgctctccg cggccttctg gcctatcttc ctgtggctgc tcagcgcccg     1560
tttctccgtc ggtctgcgta aagcggccgt tattaccggc tatgttctgg ccgccgtggt     1620
gggctattcg cggctggtca tccatgcgca ttccgtctcg gaagtgattg ccggcctgct     1680
gctgggcgct gctggcagcg cttttgttcct ggtgttgcaa aaacgtacct ctgatccgga     1740
aagcgtgaat atctcatggg gcggtgtcgc atgcctggtg atggtccctc ttatcctgtt     1800
acatagcggc agcaaagcgc cgactcagtc cctgctggga caaatcgcca ccgcggtggg     1860
gccgctggat aaacccttta cgcgtaccga tctgcacaag caggcctggt aatcgccatt     1920
tgttttacag gggaaattaa gttttcgccg gttaattaga caaataagaa aataatctac     1980
tatatacccg gtaattgata attcatattt atgaaataat gaagtgctac tacattgtta     2040
ttgcatattt gtctggatat agctttgatc agacgtttct taaatgcgct gagacgttac     2100
ccgatgcaca ttcaatgaat atccagacac aggaaactat tagaaattgt agttgactat     2160
aacgccatca tctgatttttt gcatgaagat gagctatgga aaaagacgtt ttattacagt     2220
cagttagctg catgtgtgat gttgtagcag taccggaaag atttctaacc ctggaaatca     2280
gtgaataatc ttaattggtg acccgcttat tttttgtcag tagaacgaca ggcggcatta     2340
attggcagat attcggtaac aacactccca attgtgaccg aaatcccgta aacttaatgc     2400
cgccaaaaat aatggcctga ccaattattc atccacaggt cgataaaaat taagccgttc     2460
aggtagtcag tgcgctggta gctgttaagc caggggcggt agcgtcgctg aagccgcttg     2520
```

```
ctgctgcaca gaggttctct tcaacggctg taaatatcga cccggtcagg atgatcatca    2580
tcaatagata tctatcaatt ttctacggat atcctcacaa gttggccagg agcggctgct    2640
gttatcgcct ggacattaac tttcctgtct catcgatagc ctgtagggta aaattcgcct    2700
acattgtgag ctgagtggat gttataaggc taacaagcag cttagggtaa atgtacttgc    2760
ctcgccggtg ttgcacagcg aagtcagctg gtgccgcgag cgctttctat cttggtattc    2820
ccctcattct cattgagata cgacagcggg gctgaaaatg gatcttgtac aatgataaaa    2880
attgcgcgca ttgccgtgac gttgggtttg ctttcctccc tgggagccca ggcttacgcg    2940
gccgggttag tggtaaatga caacgacttg cgtaacgacc tggcctggct ttccgatcgt    3000
ggggtcatcc atctgagcct gtcgacttgg ccgctgagcc aggaagagat ctcccgggcg    3060
ctaaaaaagg ccaaaccgtc ctattcttct gagcaagtgg tgctggcgcg tattaaccag    3120
cgactgtctg ccttaaaagc ggatttccgg gttaccggct acacttcaac cgatcagccg    3180
ggcactccgc agggg tttgg tcagacacag ccggcagata actcgttagg cctggcgttc    3240
aacaacagcg gcgagtggtg ggatatccac ctgcagggta acgtcgaagg aggggaacgg    3300
atcagcaacg atcgcgctt caacgccaac ggcgcatacg gcgcggtgaa gttctggaac    3360
cagtggctct cttttggtca ggttccgcag tggtgggggc cgggctatga aggtagtctc    3420
atccgcgggg atgcgatgcg gccgatgacc ggcttcctga tgcagcgggc agagcaggcg    3480
gcgccagaga cctggtggtt acgctgggtg gggccatggc agtaccagat ctccgccagc    3540
cagatgaatc aatataccgc tgtgcctcat gccaaaatta cggtggtcg ttttaccttt    3600
tcaccattcc agtctttaga attaggcgca tcacgcatta tgcagtgggg tggggaaggg    3660
cggcctgaat cactcagtaa cttctgggat ggtttaacag gcaaggataa taccgccgca    3720
aacgatccca atgaaccagg gaaccaactg gccggttttg actttaagtt caaactcgag    3780
ccgactcttg gctggccggt gagcttctac gggcagatga tcgcgaggga tgagtctggt    3840
tttcttcctt cagcaaatat gttccttggc ggtgttgaag ggcaccatgg gtggggcaaa    3900
gatgcggtta actggtatgt ggaagcgcat gacacgcgta ccaacatgag ccgaaccaat    3960
tacagctata cccaccacat ctataaagat ggttattacc aacaagggta tccactgggg    4020
gatgcaatgg gtggggatgg tcaactcatt gccgggaagg ttgagctgat taccgaagat    4080
aaccagcgtt ggagtacacg cctcgtttac gccaaagtta accctgagaa ccagtcgatc    4140
aataaagcat tcccccatgc tgataccttg aaaggtgtac agctaggctg gagcggcgat    4200
gtttatcagt ctgttcgtct gaatacctct ttgtggtaca caaacgcgaa caacagcgac    4260
agcgatgacg ttggggccag cgcagggata gagataccgt ttagtttata aggctgaatg    4320
ctgaaaatag aggagagagg gtggtagtgc tgcaggaggc agtcagtttt tatctctcca    4380
caagccggca ggtaagcaac ggcgatgaca gctgctcagg aattggcaaa ttttgattta    4440
ctgatgatgt gacattatga agaaaaaaat tgttagattt tcggcattag cgttggcgat    4500
tgggttttta tcgggttgta caatcatccc tggtcaggga ttaaacagtc tgcgcaagaa    4560
cgtggttgag cttccagaca gcgactacga tctggataag ttagtgaacg tgtatccaat    4620
gacaccaggc ctgatcgatc agctccgtcc agagactgta ctcgctcgtc caaacccaca    4680
gctggataat ttactacgca gttatgaata tcgcatcgga gttggcgatg tacttatggt    4740
cactgttttgg gatcatccgg aattgacaac gcctgcaggc caataccgta gcgccagcga    4800
cactggtaac tgggttaatt ccgacggcac gatattctat ccatatatag gtaaagttca    4860
ggtggctggt aaaacaatca gtcaggtacg ccaggatatt gccagtcgct tgacaacata    4920
```

```
tatcgaaagc cctcaagttg atgtcagtat tgctgccttt agatcgcgaa aaacgtatgt   4980
tactggtgaa gttatgaagt caggccagca gccgattacg aatatcccac taactgtgat   5040
ggatgcaatt aataatgctg gtggtctggc acctgatgct gactggcgca atgttgtatt   5100
aacacataac ggtaaagata cgaaaatttc tctatatgcg ctaatgcaaa aaggcgattt   5160
gtcgcaaaac catcttcttt atcctggtga tattttgttt atccctcgaa atgatgatct   5220
gaaagtgttt gttatggggg aagtagttaa acaagcaact atgaagatgg atcggagtgg   5280
gatgactttg gctgaagcat taggtaatgc agaagggatt tcacaggcaa tgagtgatgc   5340
tacaggcgta tttgttatcc ggcagttgaa aggggataaa caaggaaaga ttgcaaacat   5400
ctaccaatta aatgcacaag atgcatccgc tatggtgttg ggcacagagt tccaactaca   5460
gccttatgat attgtttatg tcactacagc tccgttggtc cgttggaatc gagtaatttc   5520
acaactcgta ccgaccatta caggggtaca cgatatgaca gaaactggta agtttataag   5580
gacttggtga taaagatgtt taattcagtt ttagtcattt gtacagggaa catttgccgt   5640
tcaccgattg cggaaagatt gctgcaaaaa ctgatgccaa agaaaagat agcatcagca    5700 ggtgttggcg ccttaatagg gaattcagct gaccccttcgg caatagccgt agcagagaaa   5760
taccatttat cattagatgg tcatgttggt aaacaactgt cgtcatctat ggctcgtcaa   5820
tatgatttaa tattggttat ggaaaaacac catcttgaac aagtgactca tatatcccct   5880
gaatcaagag gcaagacaat gcttttaggt cactggatgg gagggaaaga aatccctgat   5940
ccataccgca aaagtgatga ggcatttgat ttagtatacc aattaattaa tcaagcatgc   6000
cgcagttggg cagaaaagat gggtcaataa cttcaggata aagtgcatgg catcggtaac   6060
gaataacaaa caaacaccta ccgaatcgga tgatatcgat ttaggtaaaa ttgtcggtga   6120
gttaatagac catcgcaagc taattattgc tatcacaaca gcttttacgg ttatagcagt   6180
gctctatgca ttactagcga ctccaatata tcaatcaaca gcactaattc aggttgagca   6240
aaaacaaggt aacgccattt tagatagcct gagtcagatg cttcctgata gccaaccaca   6300
gtcagcgcct gaaatagcat taattcagtc tcgaatgata ttagggaaaa ctgtagatga   6360
tctaaattta caagcagaaa tcgagccaaa gtatttcccg atatttggac gaggtttggc   6420
aagattgctg ggtaaagagc ccgggactat atcagtccca agattctatt tagatacagg   6480
aagtaatgat gtaccctctg aggttacttt aactatcttg ggtgagaata attttgaaat   6540
tgagggggaa ggattttctt taaaaggtaa aaagggtgtt ctgttggaag ataagggagt   6600
ttcaattctc gtagactcta tcgatgccca acctggaagt caattcaaaa taacctatat   6660
aagtcgtttg aaagctatta gcaacttgtt agagtcatta aatgtagcag accaagggaa   6720
agatactggg atgttaaatt tgacttttac aggcgataat ccgactttaa tatcacaagt   6780
tttaagtagc attactcaga actatcttgc gcaaaatgtt gaaagacaag cagcgcaaga   6840
tgcaaaaagt cttgagtttc tgaatgaaca attaccaaag gtaagaactg atttagacgc   6900
agctgaggat aagttaaata actatcgtaa gcaaaaagac tctgttgatt taacaatgga   6960
ggctaaatct gttttggatc agatagtaaa cgttgataat caacttaatg aacttacttt   7020
cagagaagcc gagatttctc agctatatac gaaagaacat ccaacttata aagcgttaat   7080
ggagaaaaga caaacattac aaacggagag gaaaaaatta acaagaaag ttagctcaat    7140 gccctcgact caacaagagg ttttgagatt aagcagagat gttgagtccg gtagggctgt   7200
gtatttgcaa ttgctgagcc gacagcaaga gctaaatatt gccaaatcta gtgctatagg   7260
taacgtacgt attattgata atgcaattac tgaaccaaaa ccggtaaaac ctaaaaaaat   7320
```

```
tcttgtgatt gctttaggta ttatcatcgg gttattcttt tctgtaggtt ttgttttcgt    7380
cagagtattc ttgcggagag gtatcgagtc ccctgagcag cttgaagaaa tgggaatcaa    7440
tgtatacgcg agcatccctg tatcagaatg gcttactaaa aacactaata aaaataaaag    7500
acaaaaaaat gaatctgata cattgttagc tgttgaaaac ccagcagatt tggctgttga    7560
agctatcaga agtttaagaa ctagtcttca ttttgcaatg atggagtcga aaaataacat    7620
attaatgatt tctggagcta gtcctaatgc gggtaaaaca ttcgtaagta cgaatttagc    7680
cgctacaatc gcgatgacag gaaagaaagt tcttttttatc gactctgatc tccgaaaagg    7740
atacgttcac aaaatgttgg gttcggaaaa tgtcaaaggt ttatctgata ttttatctgg    7800
ccaagcgaaa gttgaaagta ttatcgaaag agtcagtggg ggggaatttg attatattgg    7860
tcgtggacaa acaccaccaa atcctgcaga gttgctgatg catcctcgat tcaaggaact    7920
attatcttgg gcatcgcaga actatgaatt agtaattgtc gatacgcctc caattttggc    7980
tgttaccgat gcggcaataa tcgggcaata tgctggaaca actctacttg tagctcgttt    8040
tgaagcaaat acagctaaag aaattgctgt aagtattaaa cgcttcgaac aaacaggcgt    8100
agttatcaaa gggtgtatct tgaatggtgt aatgaaaaaa gcgagtagct attatagcta    8160
tggctatagc caatatggct actcatatac agataataaa tctaaataaa aaattattgt    8220
ggccgttgta tggccacaat aatgtctatt ttgcattaac atcataagta ggcgtgtaac    8280
tatgacactc tttacaaaga ataaagttg cagtatatca ttagtgataa cggacttctt    8340
aagctttgtc ctgtcacttt atttttctgt ttttattttg tctttaactt taaataattt    8400
tgatgctcga gttccgaatg atcaattaga aggatggatt gcacttcatt ggttactcgg    8460
ggtctgttgt gtggcttggt atggaataag attaaggcat tatttctatc gtaaaacatt    8520
ttggtttgag cttaaagaaa tattgagaac attagttatt tttgctgtta ttgaaatggc    8580
tgtgatggca tttgcaaaat ggtatttctc ccgctatgtt tggttgttaa cgtgggttat    8640 ggcaatatt ctcgtaccat tagctcgtat tgccataaag tggttgttga tgaaatgggg    8700
tttatggttg cgagatactt ggattattgg aagcgggaaa aacgcttatg aagcttataa    8760
agcaatctca agcgagcgta atctcggttt aaatgtagtt ggttttgtca ctgatgaaca    8820
aatgcaagga gagcaacgta aaacgattga tgagcttcca ataattatag gaaatatcga    8880
ttggttaaat aataaagata acgaaccca atttatcgta gctgttgaat ctgaacaaag    8940
tgatattcgc aacaaatggt tacgcgagtt catgatcaaa gggtatcgtt acgtttcggt    9000 aataccctacg ttaagaggga tgcctctgga tagtacagat atgtccttca tttttagtca    9060
tgaagttatg attttccgtg tccaacagaa tctggcgaag tggtcatctc ggataattaa    9120
gagatgtttt gatattttcg ggtctatttg cataatattg atgttatcac ctcttctttt    9180
atatatatat atgaaagtta aaaagacgg cggtcccgct atttacggac atgaacgagt    9240
gggtattaat ggaaagacat ttaaatgcct caagtttagg tctatggttg ttaattcaaa    9300
ggatgtatta gatgaattat tgaaaaatga ccctatagcc aaagaagagt gggatgcgac    9360
ttttaaatta aaaaatgatc ctaggataac aaaaattggt gcttttctgc gtaagactag    9420
tctggatgaa ctgcctcaat tatttaatgt tttgaaagga gagatgagtt tagttgggcc    9480
gcgaccaata attaatgctg aattagaaag gtataatgat caagttgatt attatctttt    9540
gagtaagcca ggcatgactg ggctttggca ggttagcgga agaagtgata ttgattatga    9600
tacccgtgtt tatttggacg catggtatgt taaaattgg tctatgtgga atgatatagc    9660 catacttttta aaaactgtca cagtagtgct taaaaaagat ggtgcatact gattcattat    9720
```

```
gcttggataa aaacaatgaa taatgtggcc ctgaaagaaa agactataac aagtcttatc   9780
tggaatgcga tcgaaagatt tatggtacag ggagggcaat ttgtaataaa gattctaatt   9840
gcccgacaaa tctctcctga cgattatgga ttagtaggaa ttgttgctgt attttagtt    9900
ttgtcggacg taattattaa tgggggattt tcgcaagctt taatacaaaa aaaagataga   9960
acatctctgg attactcaac tgtcttttat ataaatatat ttgttgcaat actattatat  10020
cttgctctct ttttcttctc acctttaatt tctgacttt  ataatgatca gagattaact  10080
gatataataa gattaatttc tattagtata gttataaaat cattaagcgt tgttcagttg  10140
gcaaaaataa gcattgaatt aaatttcaaa gctaaaacaa ttgttaattt ctgggcggtt  10200
ctaattagtg gttttattgc agtatatatg cttataatg attggggagt atatgcatta   10260
atctatcaaa ccatattata ttcaataatt gtgaccgttc taatgttttt cattgccaaa  10320
tggactccaa aactagagtt ttcaatggca cgggcatata gtttattcag ttttggatca  10380
aagatattct tggccaatct agttggtgtg atttcagaca actcatacgc tattcttatc  10440
ggtaagctat tttctagtaa agaagttggt ttttttacgc aagggagaaa tcttcctgac  10500
ttgttatctg ttaatctttt caacatatta caaggagttc ttttcctgt  aatgtcatct  10560
gcacaggatg acaaagaaag gttgttaagg atataaaga aaagtctaaa tatgactgca   10620
tttattgtcc tgccatctat ggttgggtta gtaattattg ccgagccatt tgttagagta  10680
tttctgactg aaaaatggtt gccgagtgta tttattattc aatggcttgc attatcaaga  10740
atgattgttc cattaggtgc tattaatgca aatttgctaa attcaattgg caggtcagat  10800
ttatatctta aaattgactt aattaaactt cctcttacta ttctaggatt actgatctcc  10860
tcaccatttg ggttacaata tatggtaatc agtaacttta tagtagcaat attttattat  10920
tttattaatg cgtattatcc aggcaaaatc ttcaacttcg ggcctatatc gcaactgcta  10980
aacatgttcc caattatagt ttctacgagt gttatgtttg tcgcgacata ttttggtca   11040
atcaacaatg gcttgttaga cattattatc aagatcgtag tcggtgcgat agtatacatt  11100
atttcctgct ttgttctcaa agttgaatct gttaaggaaa tttggtccta tatgctaggt  11160
aaaattaagg gaaaaacag gagaagtact tgtggctaat gtaatcattt ttactaatga   11220
atattttccc ttcaaaggag ggatcgggcg ctactgtgaa gaagttatta atgaaataaa  11280
acttcagcac aaggttacgc ttgtggggcc tgcgtacgat tcatctttga ctcgcgataa  11340
acgttctgaa ggaatccgtt tagagctttt tcctggtggt caatttaagt attggcattt  11400
gccaaaactc atcaagaaag tgagctcgat cgattttgaa caatatgatt atgtcttggt  11460
tgcagattgg ccattctggg tagcaattga atttttgaat agatttagtt ttaaacggaa  11520
aattcgtttt aatttaatgc tacacggtag cgaagtgtta aacttgaaat ttgggcgagc  11580
ttccatcttt agtaaaatac taaacatgtt tgatggggta aagaaaatat ttacaaatag  11640
caattataca aaaaaaattc ttttagagta tcatcaagta cccaaagata tatcgattat  11700
tacaacttat ttaggtgtta atgaaagtga gttcgctaga aacaatgtct ttctaaaaaa  11760
cgttaacaac gaaacattta atatattatc tgttggaaga cttgatgaaa gaaaggatt   11820
cgataacgta ataaaagcat tagggatgct ggataatgat gttaaacaac atataaaatt  11880
tacaatagtt ggaaatggca gtttagaatt caagggatat ctaaaaacct tagcaaaaga  11940
aaattctgtt gatgtagaga ttaaatctgg cgtctctgac tctaaattaa acgagttata  12000
tggcgaagcg aatttatttg ttttggctgc gaaatctagt aataaaaaaa ttgaaggatt  12060
tggattggtt tttcttgagg cggctaaaca tggagtccca tctctagcaa cagatgtagg  12120
```

```
cgctattagt gaggtcgtaa aaaatgaaaa cactggtctt gtagtcaaag aagatatttc   12180
agaattatcg caggctatat atcgctgcta tactcataga gatctgttag ttaaatttag   12240
taataattgc gttaatgacg ttgctaatta ttcatgggca aaactagcag atattacttt   12300
ctcagatatc aataataagt aaggattact atgtctaatt taaaagttct ttttgtagat   12360
acttgtcacg atgttgctgg gggacagcga agtttgattg cactattatc taacgtaaat   12420
agtaagttca agtataatgt tatgatacat aatggtaata aaaaatacct aaatgaactt   12480
cttgcgaatg gcgtgcctcg tgagaatatt attttgatta ataccaagcc gctcggttta   12540
aaaattcttg gtggcgttaa actgttttc aaatgcatga cattagcaaa aaaatattca   12600
ctaatgcatt gcaatacttt ctttgatggt ttatttgcta tgccttcttt tagattacag   12660
gctaaaaaaa ccatctttcg tgcacgttgt ggaattgacc tttctaatca tggcatcgtt   12720
gataatgtaa tttatcacaa tgcgtctgta atactcgcta actcagagta tgttaagaca   12780 acttttcac ggataaaattc aaatcttgcg aaaattgatg tcatttataa tcctctagat   12840
ctcaagtttt atcgagaatt caaaaatata acgaatgaaa aaagaaaat aattgctgta   12900 attggtgcta taactgaagt aaaaaaatcag atggaagtac ttaaagcatt ttcacttatt   12960
aataatgaaa atatattctt acggtttata ggtgaaccta gaagtactga taaagataga   13020
ttatacaatg atgagttaat gtcttttatt aaaaaacata acttagagaa taggattgag   13080
tttagtggtt tcgtttcaga cgtaagaacg caacttcaag atgtggatct tgtttgtgta   13140
ccatcggatc gtgaaccatt aggacgggtc attttttgaaa cacaattgtt taacattcct   13200
gttttagcat caaattcagg tggtaatgga gaattaataa ttgatggtaa aactggatat   13260
ctatatgaat taggtaatat cgaccagttg aaagaaaaaa tgttaaaagt aaattctcca   13320
aatgagaaat taatcaatga tgctcaaaaa ttcgttctag aaagattttc accagacaaa   13380
acttaccttg ctgaatttga gctctatgaa agactttctc gataaggatt atcttaaaaa   13440
tgcagacagt aaataaaaat agcattgcgt tatcacttat ttatttagcc attgtcataa   13500
ttacgttaat acccttggga cgtggtaata tctcagggct agaagtgtca tttcctttt   13560 ttattttgc tattttttt ctgcttgtaa aaaaaaataa agtgtatgat attacgtttt   13620
ttgcaaacct tttttttaca ttatgggctg tatgggtact ttgtggtata acctacagct   13680
attttacatt cccgggggg gttgatcatc aggcgtcgta tctcaggtat attcggctgt   13740
tggaaatgta tttgccagga tgtatgattt tatctttcct tggtgagcta cccaattctg   13800
ttcataaaaa gatagtctat ttacttattc ttttatttgt tattgttact ctggaagcga   13860
cagttggttt tgtatcacaa agtgatttgc tcactgctac tcagatgtat aaatacccctg   13920 gcttcggtta tgtatttcgt gctggaggg tcgctaagga ttctagtgct tatggcagcc   13980
ttgttttttt attagggatc actgcattaa ttgagttaag gaaaattaga acaaataata   14040
gattgttgtc gtttattata atttcgtgtt tattaattaa tatatatata tctatgtcac   14100
ggagcttaat tgtatctgtt gcattatact ttttgatata tatatgtatg gagaagaaat   14160
ctcgagttaa atcatttctt atcctaggag tagtgtcttt atttattttt atgtatggac   14220
ttacaaatga atattttta tcattttaa atagattgac aggggggagag caaacagaca   14280 tcagttccgg acgattttca acttgggctt cttttgcttgt acttattgct gaaatccta   14340 ttttcggtgt tgggtataga ttaactacag aaaagtataa tttaataccg gataatatgt   14400
ttctttcatt attggtagaa acgggaataa ttgggtttat attatacttt tcattttaa   14460 cctgcttgct gatttatgtt ataaaatata atcgagataa gttcccattg cttgtggcat   14520
```

```
atatattctc tggcttttt  atcgacatct cgactttctg ggttagtgtt cctgttttat    14580
tcttcgtttt agcaattcgg agtgttggca acgaatagtc ttatttgtga ggtgtgtatg    14640
agagaagcaa tggcactatc tgaagataag tatcttatca ctcgcagaaa attgctctta    14700
ttatcattac cttttggtta tgcaatagtt aatgagagca aagcaaattc taactcgcct    14760
ataaaggtac ttaatgtttt aaatttcgga gcaaaaggtg atggaataaa tgatgattct    14820
tacgcttttc aacaagcctg taatactgct agttctttgg gggggcgaa  attatatata    14880
ccaccaacaa aagaatatta tagaattcta ttccctgtat atattggcga taatactgaa    14940
ttgttcggag agggacaaac aacaagaata gtctttgaaa atccaatatt taataaaggg    15000
cggggaggat tcgttatagg atcaagttta gaagctaata gacatctagc ctttaagagg    15060
tattctaatt ttactcaaga gacgacgatt aatcctgatt tcaaaaccc  caaacagaaa    15120
caatacttaa gagataatcc tcattttatt caggcggaaa atagtagtat tcatgacctc    15180
tatttagagg cgagatttac taatagtaca aaaaataaat ggggagggta tggcatcaac    15240
tttgtcaatg ctcagaattg tcatgtttat aatatatggg gaaagggatg gactcaattg    15300
atcgggatgg gatcagatat tccacctgag actccctcaa atcatttatg ttctgccaaa    15360
tatttacatg tgttggaacc ggatttggtg agaacctatt attctatagg tttcattgca    15420
aattctacag actgctcaat agaacacgca atacaatacg taccgatgac aagcggttca    15480
ttaaatggaa gtggtgctgc tctaaattta tgcgaagatt gtcttatcag taatattacg    15540
attcctcact tggggaaaac tcaaacctct gaagggatta tggttaataa ctcttctggt    15600
tgtcgtgtta ataatattat gattggtgat gctaaaattg cggtgtcttt attctttagc    15660
gacaaatcta ctcttaaccc tgaaaaacct aattttatag ataccgtaac aggcgtaaat    15720
tgtaattcag taatttcggt ttttctaaa  tataattata ttaaaaatat aacggcgaaa    15780
gactgtattt ataaagttgt tttgaaaaat agaaacgcaa ctaataacca ttttgatttg    15840
cctgctagtg aaattgttac agcaaacact aaagatgctg attttttatt aaaaaacaac    15900
actttccaat aatctagtaa atgagaactt agatgggtaa aaatatcaaa gagcgcaatc    15960
aattagctga ttttgccagg gttttatgg  cttttattgt tgtggctatc catgttaata    16020
tttttttatga acatcccgcc ctcaataaaa taactgttga tggtttttt  agaattgcag    16080
ttccttttt  cttaatgata aatggatatt attttcatga aaatatttcg catgttgaaa    16140
gcttcaagaa atggctaaaa agaggtatcg tttttatttt cgtttggcaa gcggcttttgt   16200
tgaataaatc gaacttttgc tgagttgaag gatcagatca cgcatcctcc cgacaactca    16260
gaccattccg tggcaaagca aaagttcaga atcaccaact ggtccactta caacaaagct    16320
ctcatcaacc gtggctccct cactttctgg ctggatgatg aggcgattca ggcctggtat    16380
gagtcggcaa cgccttcatc acgaggaagg ccccagcgct attctgatct cgccatcacc    16440
accgttctgg tgattaaacg cgtattccgg ctgaccctgc gggctgcgca gggttttatt    16500
gattccattt tgccctgat  gaacgttccg ttgcgctgcc cggattacac cagtgtcagt    16560
aagcgggcaa agtcggttaa tgtcagtttc aaaacgtcca cccggggtga atcgcacac    16620
ctggtgattg attccaccgg gctgaaggtc tttggtgaag gcgaatggaa agtcagaaag    16680
cacggcaaag agcgccgtcg tatctggcga aagttgcatc ttgctgttga cagcaacaca    16740
catgaagttg tctgtgcaga cctgtcgctg aataacgtca cggactcaga agccttcccg    16800
ggccttatcc ggcagactca cagaaaaatc agggcagccg cggcagacgg ggcttacgat    16860
acacggcttt gtcacgatga aatgcgccgc aaaaaaatca gcgcgcttat tcctccccga    16920
```

```
aaaggagcag gttactggcc cggtgagtac gcagaccgca accgtgccgt tgctaatcag    16980
cggctgagcg gaagcaatgc acggtggaaa tggacaacgg aatataaccg tcgctcgata    17040
gcggaaacgg caatgtacag aatgaagcag ttgttgggag attcactgac gctgcgtgac    17100
tacgatggtc aggtagcgga agctatggcc atggtgcgtg cgttgaacag gatgacaaag    17160
gctgggatgc cagaaagcgt gcgtattgcc tgaaaatcca gccagctaca gggtcgttcg    17220
cacgaaatct tatttattca acaaagcctt ggcaagcaat ctatttacct ttataccttc    17280
cgattgaaga tttaagttat aatcgattgg cggttttctt atcgcaactt atatttggct    17340
atcatcacct ttggtatata agtgccatgg tgcttggtgg tattatactt tttgcacttc    17400
gtgataaacc atattcatta gctttgagtt tattttatt cattatcggt tgctgtttgc     17460
aatatgtgcg acctttata gataacaatc cgacgctata taaagttttt tctcaatatt     17520
ggttgttccg taatggcctc ttttttggct ttccaatgat gtctatcggt ttttatattg    17580
caaaaaataa tcttcttatt aaatttaata ataattttt gttttgttt ttgtctattt      17640 caacaatatt gtatggttgc gaaatattct ttgtgcaaaa tattttttc tcacatatga     17700 gttaccatat tgattttta ttgtcaattc tcttgttgac gccagttgtt tttattttta    17760
tcatgcgaac gaaattttgt ccttttaaag ataaagacac taaatattta gccttgttta    17820
gtagtatcgt atatttatc catccctatg tgatcaagtt aattgaatct tttctttcca     17880
tagaaagtgt tatgttttat atcaatgtct tagttatatc atctctaatt agtttcttct    17940
gtgttttgaa taggaaaaga ttatggttcc tattctaaat aaatctttat ttcttatagt    18000
ttttattaat tcttcaatct ctctttaata gctaattgcg attgaaatag taaaccgcaa    18060
tttgcctttc cttatggata atggatctta tatgcaagaa ttaaatgttg gtattgttgc    18120
cgactggttt ataacttatg ccggttctga aaaggttgtc gctgaatttc tggatgtttt    18180
tccagaggct gaattatatt cggttgtcga cttcttatct tctgaaaata aatcccattt    18240
caagaataaa aatattacta ctacatttat tcaaaacttt ccttttgcaa gaaagaaata    18300
ccaatcatat ttgccttta tgcctcttgc tattgagcaa ctagatgtat caaaacatga    18360
cgttattctt tcaagttccc atgcagtggc gaaggggggtt ctcacaggcc cagatcagtt    18420
acatataagt tatattcatt caccaataag atacgcatgg gatcttcagc atcagtactt    18480
gcgtgaatct aacttgcaca aaggttttaa agggttgtta gcgaaatgga ttctgcataa    18540
tatacgcatt tgggattgtc gcacgtctaa tggtgtcgat cattttattg cgaactccaa    18600
attcatagca agaagaatta aaaaagttta tggtcgtaat gctgatgtta tatatccacc    18660
agtagatgtt gaaagattta cactcaatga gaacaaagaa caatattatt ttacagcatc    18720
tagacttgtt ccctataaac gcatagattt gatagttgaa gcatttagtc atatgaagga    18780
taaaaagcta gttgttattg gtgatggacc tgagatgaat aaaataaaag ctaaagcaac    18840
atcaaatata gaaatacttg gctaccaatc taatagcgtt atggtcgact atatgagaaa    18900
tgcgcgggct tttgttttcg ctgcagaaga ggattttggc ataactcctg tagaagctca    18960
atcttgcggt acgccagtaa tcgcttatgg aaaaggtggt gctcttgaaa cgatacgacc    19020
catcggagtt gaaaaagcaa ctggtgtctt tttctataat caagatgtca agtcaataat    19080
cgatagcgtt aatttttttg aacagcatag tgatgaaatt attctctctg actgccgtct    19140
gaacgctcta aaatttctg agcaaagatt taagaagag attaaagaat atgttatgaa    19200
tcggcatgct gaatttttag cctctaaatc tgtcgtatat taatttttta aattcaaata    19260
gtaaatatgt tttgtttgat gacagtatga gtttgatcat atatgatatg cgtgaagtta    19320
```

```
gttatatgct aatataggta tatataaccc tgtaatttta cagtgatttc accagacagg   19380
agtttgtaat gtccaagcaa caaatcggtg ttgtcggtat ggctgtgatg gggcgtaacc   19440
ttgcgctgaa tatcgaaagc cgcggttata ccgtatccgt tttcaaccgc tcccgtgaaa   19500
agaccgaaga agtgattgcc gaaaatccag gcaagaaact ggttccttat tacacagtac   19560
aagagtttgt tgaatccctc gaaacacccc gccgtatcct gttgatggtg aaggcagggg   19620
ctggcaccga cagcgccatc gattccctga agccttacct cgacaaaggc gacatcatca   19680
ttgatggcgg caacaccttc ttccaggaca ccatccgtcg taaccgtgag ctgtctgccg   19740
aaggttttaa ctttatcggt accggtgttt ccggtgtgga agagggggct ctgaaagggc   19800
cttccatcat gcctggtggg cagaaagaag cctatgagct ggttgctccg attctgaagc   19860
agattgctgc ggttgctgaa gacggtgagc catgtgtgac ctatatcggt gctgacggtg   19920
ctggccatta tgtgaagatg gttcataacg gcatcgagta tggtgacatg cagctgattg   19980
ccgaagctta tgcgctgttg aaaggcggtc tggcactttc caacgaagag ctggcgcaaa   20040
ccttcaccga atggaacgaa ggtgaactca gcagctacct gatcgatatt accaaagata   20100
ttttcaccaa gaaggatgaa gaaggtaagt acctcgttga tgtcattctt gatgaagctg   20160
caaacaaagg caccggcaag tggaccagcc agagctcact ggatctcggc gaacctctgt   20220
ctctgatcac cgagtccgta tttgctcgtt acatctcttc gcttaaagac cagcgtgtag   20280
ctgcttcgaa agtgctgagt ggtccgcacg ctcagccggc cggcgataaa gcagaattta   20340
tcgaaaaagt tcgtcgtgcg ttgtacctcg gtaaatcgt ttcctatgct cagggcttct   20400
cccagctgcg tgccgcttct gatgaataca actgggatct gaactacggc gaaatcgcta   20460
agattttccg cgctggctgt atcattcgtg cgcagttcct gcagaagatc accgatgctt   20520
atgcgaaaaa cgctggcatt gctaacctct tgctggcgcc gtacttcaaa cagatcgctg   20580
atgactatca gcaagcgctg cgtgatgtcg tggcttatgc cgtgcagaat ggtattccgg   20640
taccgacgtt ctctgccgca attgcctact acgacagcta ccgttccgca gttctgccag   20700
ctaacctgat tcaggctcag cgtgattact ttggtgcgca cacttataag cgtaccgata   20760
aagagggtat attccataca gagtggttgg aataa                              20795
```

<210> SEQ ID NO 45
<211> LENGTH: 20704
<212> TYPE: DNA
<213> ORGANISM: Klebsiella pneumoniae

<400> SEQUENCE: 45

```
atggcgaatt tgaaagcggt tattccggtc gcaggactag gcatgcatat gctgccggcc     60
acaaaggcaa ttcctaagga gatgctgccg atcgttgata agccaatgat tcagtacatt    120
gttgacgaaa tcgtcgccgc cgggatcaaa gagattgttc tggtgacgca ctcctcgaag    180
aatgcagtgg aaaaccactt tgatacctcc tacgagctgg aagccctgct tgagcagcgt    240
gtgaagcgcc agctgctggc ggaagtccag gccatttgcc cgccgggcgt aaccatcatg    300
aacgtgcgcc aggcacagcc gctgggtctg ggccactcga ttctctgcgc ccgcccggta    360
gtcggggaca acccgtttgt ggtggtgctg ccggatatca ttctcgacgg cggcactgcg    420
gacccgctgc gctataacct cgctgccatg gtcgctcgct ttaacgagac cggccgcagc    480
caggtgctgg cgaaacgaat gccggggat ctctccgaat actccgttat ccagaccaaa    540
gagccaatgt tggcggaagg gcaggtggcg cgtatcgtcg agtttattga aaaaccggac    600
gaaccgcaga ccctggactc cgacctgatg gcggtgggcc gctacgtgct gtcggcagat    660
```

```
atctgggccg aactggagcg taccgagcca ggcgcctggg gccgtatcca gctaaccgac    720
gccattgccg aactggcgaa gaagcagtcc gttgacgcga tgctgatgac cggggaaagc    780
tatgactgcg gtaaaaaaat gggctatatg caggccttcg tcacctacgg aatgcgtaac    840
ctgaaagaag gcgccaaatt ccgcgaaagc atcaaaaaac tgctggcctg agcgccggcg    900
taagggtgag cggcagggca ggggtatttt gccacgccgc tcataacgtt atgcagaaat    960
tattcataac gtgaatgtta taacgattgt aaagaaacgt atggcttcgg agacttctgg   1020
tagtttgtct ctggcctctg tggtgcaatg gtcggagtag cggcaataat gctttgtgaa   1080
tagtcactta gtgcgacaat tcctaaagcg cagggaaagc ggtcaacgtc agccaaaaat   1140
aaaacttgac tgcgatcatg tttccgcttt aaacatctca cttgcatgca taaaaatgtg   1200
aaatgaattg gcatgcgagc tggtacagac attacggata atccctgagc acggcagtgg   1260
acatcatcga aggatcacag gtatatgaac tggcaactca tctcattttt tggcgatagc   1320
accgttttgc tgcccagcgc agcggcgctg tttattgtcc tgatgctgcg taaaacgtcg   1380
cggttgctgg cgtggcagtg gagtttgctg ttcggcatca ccggcgccat cgtctgcgcc   1440
tccaaactgg cctttatggg ctggggtctg ggtattcgcg agctggatta caccggcttc   1500
agcggccact cagcgctctc cgcggccttc tggcctatct tcctgtggct gcttagcgcg   1560 cgttttccg cgggcttgca aaaagcagcc gtcgccaccg gctatattct ggccgctgtg   1620
gtgggttatt cacggctggt catccatgcg cattccgtct cggaagtgat cgctggcctg   1680
ctgctcggcg ctgctggtag cgctttgttc ctgttgctac aaaaacgtac cacccattcg   1740
gaaagcctga gtatttcctg gggcggcgtc gcgtgcctgg tgatggtccc gcttatcctg   1800
ttgcatagcg gcaataaagc gccgactcag tccctgctgg ggcaaattgc caccgcagta   1860
gggccgctgg ataaacccctt tacgcgtacc gatctgcata agcaggcctg gtaattgcca   1920
tttgttttac aggggaaatt aagttttcgc cggttaatta dacaaataag aaaataatct   1980
actatatgcc agtcaattga taattcatat ttatgaaata atgcagtgct actacattgt   2040
aattgtcaat ttgcgtggat atagccgtgg tcagacgttt cttaaatgcg ttcagaaagc   2100
acctgttcca cgttggatga ataatcctgc atcgagaaac tattagaaat tgtagttgac   2160
tgtcgcgtca tcatctgatt ttggaatgac gtatgtgtaa tggaaaagat gttttttttac   2220 aaagggttat cttttcctgt gccggcatgg tggcgccagg cagatgttag gtagttaaga   2280
gcaataaata tctttattg gcgagccgct tattttcgc caataaaaca gcggatggga    2340
ttaattggca gatattcggc agtaagactc ccaattgtga ccgaaatccc gtagacttaa   2400
cgccgcaaaa aataaaggcc tgaccaattt atcacccaca ggccgattaa atacgccgtt   2460
caggtagtca gtgcgctggt agctgttaag ccaggggcgg tagcgtcgct gaaaccacct   2520
gttgctgcac aaatatcttc tctgaacggc tataaaaatc gatgcacttt gggtgattga   2580
cgccataaga tatctatcaa gcttatcaga tatcctcata aatgggtcag gagcagctgc   2640
tgatatcgcc tgtataccaa ctttcccatc tcatcgatag cctgtacggt aaaattcgcc   2700
tacattgtga gctgggtgga tgtgaaaggg tgacaagcag cttagggtaa ctgtacttgc   2760
ctcgccggtg ttgcacagtg aagtcagctg gtgccgcgag cgctttctat cttggtattc   2820
ccctcattct cattgagata cgacagcggg gctgaaaatg gatcttgtac aatgataaaa   2880
attgcgcgca ttgccgtgac attgggcttg cttttcctcac tgggagccca ggcttacgcg   2940
gccgggttag tagtaaatga taatgatctg cgtaacgacc ttgcctggct ttccgatcgc   3000
ggggtcatcc atctgagtct gtcgacctgg ccgctaagtc aggaagagat cgcccgggcg   3060
```

```
ctaaaaaagg ccaaaccttc ctattcttct gagcaagtgg ttctggctcg aattaaccag    3120
cgactgtctg ctttaaaagc cgatttccgg gtcaccggct acacctcaac cgaccagccg    3180
ggcactccgc aggggtttgg ccagacgcag ccggcagata actcgttagg tctggcgttc    3240
aacaacagcg gcgagtggtg ggatgttcac ctccagggca acgtcgaagg gggagagcgg    3300
atcagtaacg gatcgcgctt caacgccaac ggcgcctacg gtgcggtgaa gttctggaac    3360
cagtggctct cctttggcca agtaccgcag tggtgggggc ctgggtatga agggagcctg    3420
atccgcgggg atgcgatgcg accgatgacc ggattcctga tgcagcgagc cgagcaggcg    3480
gcgccggaaa cctggtggct gcgctgggtg gggccatggc agtaccagat ctccgccagc    3540
cagatgaatc aatataccgc tgtgccgcat gccaaaatta ttggtggccg ctttaccttc    3600
tctcctttcc agtcacttga actaggtgca tcgcgcatta tgcagtgggg cggggaaggg    3660
cgaccgcaat ccttcagcag cttctgggat ggctttacag ggaaagacaa tactggaacg    3720
gataacgagc cggggaacca actggccgga tttgacttta aattcaaact cgagccaact    3780
cttggctggc cggtgagctt ctacggacaa atgatcggtg aggatgagtc tggttattta    3840
ccatcggcca acatgttcct cggtggagtg gaagggcacc acggttgggg taaagatgcg    3900
ataaactggt acgtggaagc acatgacaca cgcaccaata tgagccgaac caattacagc    3960
tataaccatc atatctataa ggatggttac tatcagcagg gctatccgct aggtgatgcg    4020
atgggagggg atggtcagtt gttcgctggc aaggttgaac taattactga ggataaccaa    4080
cgctggagca cacgtctggt ttatgccaaa gtcaatccta aagagcaaac aattaacaaa    4140
gcatttcctc attctgacac gcttaaaggt gttcagctgg gttggagcgg ggatgtatat    4200
cagtcggtcc gtttgaatac ttcactgtgg tacaccaatg ctaacaacag cgacagcgat    4260
gacgttgggg ccagtgcagg gatagagata ccgtttagtt tataaggctg aatgctgaaa    4320
caggggagag agggtggtag cgctgcagga tgcagtcagc ttttatctct ccataagccg    4380
gcagggaagc aacggctatg acagctgctc aggaattggc aaattttgat ttactgatga    4440
tgtgacatta tgaagaaaaa acttgttaga ttttcggcat tagcgttagc aattgggttt    4500
ttatcgggtt gtacaattat ccctggtcag ggattaaata gtctgcggaa gaacgtggtt    4560
gagcttccgg acagcgacta cgatctggat aaattggtta atgtatatcc gatgactcca    4620
gggcttatcg atcagcttcg tccagagact gttcttgctc gtcccaaccc gcaactagat    4680
aatttactgc gcagttacga atatcgcatt ggtgtgggcg atgtattgat ggttactgtt    4740
tgggatcacc cggaactgac aacgcctgca ggccagtacc gtagcgccag cgacaccggt    4800
aactgggtta attccgacgg tacgatattc tacccatata taggcaaagt tcaggttgca    4860
ggaaaaacaa tcagtcaggt acgccaggat attgccagtc gtttgacaac atatgtcgaa    4920
agtccccagg ttgatgtcag tattgctgcc tttagatccc agaaaactta cgttacaggc    4980
gaagttatga agtcaggcca gcagccgatt acgaatattc ctctgactgt aatggatgct    5040
attaataatg caggtggact ggctcctgat gcagattggc gcaatgttgt gttaacgcat    5100
aacggtaaag atacaaaaat ttcactttac gctctaatgc aaaaggcga tttgtcagaa    5160 aaccatctcc tatatcctgg tgatattttg tttatcccgc gaaatgatga tctaaaagtg    5220
tttgttatgg gggaagtagt taaacaagca actatgaaga tggatcgtag tggtatgact    5280
ttggctgaag cattaggtaa tactgaagga atttcacaag cactgagtga tgctacaggc    5340
gtattcgtta ttcggcagtt gaaagggggat aaacaaggaa agatcgcaaa catctaccaa    5400
ttaaatgcac aagatgcatc agctatggtg ttgggcacag agttccaact gcagccttat    5460
```

```
gatattgttt atgtcactac cgcgccattg gttcgttgga acagagtaat ttcgcaactg    5520
gtaccaacga ttactggagt tcatgacatg actgaaactg cgaaatttat aaaggactgg    5580
ccatagttat gttttgattca atattagttg tctgtactgg aaatatttgt cgttcaccta   5640
ttggtgaacg gttttttaaga cagttattac cgaataaaaa aattgactca gctggtactg   5700
aagctttggt acatcatgct gccgatgata gtgcatccaa aattgcattg tgtcatggta    5760
tttcgttgga aggacatcaa tctaaacaat ttacttcctc attaggccgt caatatgatc    5820
tgatcttagt aatggaaaaa tatcatattg agcgtattgg gcagattgca cctgaagcta    5880
gagggaaaac aatgctattc ggacattggc taaatcaaag agaaattccg gatccttaca    5940
gaaaaagtga tgaggcgttt cactctgtct ataaacttat tgagcaagcc ggtagtcttt    6000
gggctcaaaa actaggtgca taaatcagga ataatagcat gtcatcagta actaataaat    6060
ctacgtcgaa agatgctgag ggtattgatt taggtcatct tattggtgag tttatagatc    6120
atcgaaagct gattatatca gttacatccc tctttacact aattgcactt atctatgcaa    6180
tctttgcaac tccgatctat caagctgatg cgctgatcca gttgaacag  aaacaggcta    6240 atgcgatact aagtaacctg acccagatgc ttccggatag ccagcctcag tctgcaccgg    6300
aaatagcgct tattcaatcg cgaatgattt tgggaaaaac agtagatgat ctaaatcttc    6360
aagctagagt gaaagagaag tattttccat ttccttgggcg tggttttgca cgtttaatgg    6420
gaaataagga aggaaacata tcgatatcga ggctttacat caatggcgat gatacagaag    6480
aaccaaaagt tattttaacc gttaaggata aaaataatta ttcaatccag atgggggatg    6540 ccgttttttaa cggaaaagtg ggagagctac ttgaagaaaa cgggatttca ctaaaagttg    6600
atagtataga tgctgcacct ggtaatgagt ttgttgttgc atacgtaagt agattgaaag    6660
cgataactga tttacaagat agtttgattg tagctgatca aggcaaagat acagggatgt    6720
taacattatc actaacaggt gataatccgc ttttaattga gcgtatctta aacagtatta    6780
gtgaaaacta tttagctcag aatattgcgc gccaagcagc ccaggatgct aaaagtttag    6840
agtttctaag taagcaatta ccacaagtca ggggaggttt agatcttcct gaagataaat    6900
taaatcagta tcgtcgattg aatgactctg ttgacctatc tcttgaagca aaagctgtac    6960
ttgatcaaat tgtaaatgtt gataaccaac tgaatgaatt gacctttaga gaatcagaga    7020
tatctcagct ttatacgaag gaacacccaa catataaagc attaatggag aaaggaaaaa    7080
cactacaaga tgaaaagatt aaattgaata aacgggtatc ggcgatgccg gaaactcagc    7140
aagaaatcct tcgtctcagt cgtgatgtag agtctggcag agccgtttac atgcagttat    7200
tgaaccgaca gcaagagtta aatattgcta aatccagtgc tattggtaat gttcgaatca    7260
ttgatgatgc agtaactcaa acaaaaccag tcaaaccaaa gaagatatta atcttattag    7320
caggtattgt atttggcggg atggtttctg taggacttgt gttacttaga gttctcctac    7380
gtagagggat tgaaacacca gaacagttag aagaagttgg cattaatgtt tatgcgagca    7440
taccggtagc agaaactttc acaaagaaca atttgcaagg gaaaggtaat actaaaaaag    7500
tatttaatga aattcagagc tttctagccg ttgataaccc tgctgatctt gcaattgaag    7560
ctattcgtgg gctacgaact agtctccatt ttgcaatgat ggaggcaaga aataatatcc    7620
taatgatttc tggtgctagt cctaatgcag gaaaaacttt tgttagctct aaccttgcag    7680
cagttattgc tcaaacaggg aagaaggtat atttattga  taccgatatg agaaaaggat    7740
atacacataa acttttttaat gaaaataatt caaatgggact ctcggacatt ttatctggga    7800
aaactgagat tagcttagct ataaaaacaa ttaagtcagc tggttttgac tatatttccc    7860
```

```
gtggtatggt tcctcctaat cctgctgaac tccttatgaa taagcgtttt ggggatttat   7920
tagagtgggc caataataat tatgatattg tagtgttgga tactccacct attttagctg   7980
tgactgatgc agcagttatt ggtcattatg tgggtactac tttactggta gccagatttg   8040
aattgaatac cgcgaaagaa atagaggtaa gtataaaacg ttttgaacag acaggaatta   8100
tagtgaaagg ttgtatactt aatggtgttg taaagaaagc cagtagttat tatggatatg   8160
gatataacca ttatggatat tcttatacag ataaaaagta acataaaata aagcagcata   8220
gcttgagtaa ttaatataag attactcaag cattttattg ataataatgc gttgaagtgc   8280
aaaagagag gggaatatga cgcttctcgt caggaatttt attgttagtt tttcacttgc    8340
tatatctgat cttttagtt ttgttatttc actttatctg gctgttgggg tgttatctat    8400
tacatcgagt gaatatcaaa atattttca ggctgagcaa ttagagggat ggaaggcctt    8460
gcattggtta ttggcttttt gttgtattgc ttggtattca atgcgtctac gccattactt   8520
ctacagaaag acgttctggt ttgaactcaa ggaaattta aggacgcttg taattttgc     8580
agtaattgaa atagcagtaa tggcatttac gaattggtca ttctctcgtt atctgtgggt   8640
attgagttgg actttgataa tattgttatt gcctctagct cgaatgatga caaaacgtat   8700
tctcgatatt ttcggattgt ggcgtaggga tacatggatt attggcaatg gaataatgc    8760
aattgaagct tataaagcaa ttactagtga gcgtaatctt ggatttagta tagtaggttt   8820
cattgcaagt gagcaaagta atgcaagtaa taataacatc gatggtattc cagttttaga   8880
taatgatctt aactggttat caacaataga taaaaagact caattcattg ttgcagttga   8940
gtcaaatcaa agtgaggttc gtaatacatg gttgcgtaat tttatgataa aaggctttag   9000
atatgtatcg gtaatacctg cttttgcgtgg catgccttta gatagcactg atatgtcttt   9060
tattttagt catgaagtta tgatctttcg tgtccaacaa aatttagcga aattctcatc   9120
taggatcata aaacgtcttt tcgatattat aggttcattg gcaataataa taattctttc   9180
tccagcatta gtgtatataa gtcgaaaagt aaagaaggat ggtgggcccg ctatttatgg   9240
acatgagcgt ataggtaaag gcggacattc attcaagtgt ctaaagttta gatcaatggt   9300
catcaactct aaagaggttc ttgcagaatt gctagataaa gatcctttgg caagacaaga   9360
atgggatgct acatttaagc tcaaaaatga tcctcgcatt acgaagatag gagcattcct   9420
tagaagaaca agtctagatg aattacctca gctattcaat gtactgaagg gagagatgag   9480
ccttgtagga cctagaccaa taataaccgc agaactagaa aggtataatg aagaggtcga   9540
ttattattta ctgagcaaac caggaatgac aggtttgtgg caagttagcg gacgaagtga   9600
cgttgattac gaaacgcgtg tatatcttga tgcatggtat gtgaaaaatt ggtctatgtg   9660
gaatgatata gccatattat ttaagacagt tggtgtagtg ctgaaaaaag atggtgcata   9720
ttaggtcttc ttctgaatca ttaatccaga gttaaatatg aaatattata ttgcaattcc   9780
aacatataat ggcggggaac tatgggaaaa gtccgttgct aatataaaaa aatacgcgcc   9840
tcaagatatt tttgttcaag ttattgactc aagtagtaaa gacaaaaccg tatctgtatc   9900
caaaaacgcg ggttttgatg ttataaatat ttccggaagt gaatttaatc atggtggtac   9960
tcggaatttta gcagtactaa atcatataca ggaatatgat ttggtgattt ttctaacgca  10020
ggatgctgta ccgcagccat attttatcga aaaaatagtg gatgcgttta agatagcaa   10080
cgttgcatgt gcttacgggc gacagctacc tcatcaggat gcaaatcctc ttgcgatgca   10140
tgctagaaat tataattatc cagataaaag tcatatatgt ggtaaagaaa atattccgga   10200
aatgggggttg aaaacggtat ttatgtcaaa ctctttttcc gcctatagac tttcaatatt  10260
```

```
taaagaatta ggagggtttc catctaatac cattttatgt gaggatatgt attatacagc    10320
aaaggcggtt caggctggat ataaaatcgc ttatgtcgca aatgcggtag tatgtcattc    10380
gcataactat tctccgattg aagaatttaa gagatatttt gatattggtg tttttcatac    10440
tgatgaatct tggattagaa atagttttgg gggggcggga ggcgagggag gtaagtttct    10500
tttgtccgaa ctcattttt taatcaaaaa tgcacccgca tggataccat ttgcatgcat     10560
aaataacttc atgaaaatac taggttataa gcttgggcat cattacaaaa aattgccact    10620
tagtttaaca aaaaaaatga gtatgcataa aaagtattgg gataactaat ggaaattagt    10680
tgttgtgaat tgatatatta ctgacctatc tcactaatat tgaattagtt agatctaatg    10740
agctatgtca tattgggtta tatgttagtc cattttctt ggttcggttc tttagcataa     10800
tagatattta tatttagctg atgcttcttt attgcactgt aaatttatgc aaagataaag    10860
acatggccaa ttttttattaa ccagactatt caaatagtgt tagtctggca tacaataata   10920 atatttaat caaccatcaa atgaatcaaa attgttataa ttataatctt taaccccgga     10980
tgcaattggg aatatgtcaa tcatctttga tgtatgtaga attttaaaat attaatttta    11040
atgatatgct tgaaatttta tttcaggtga ttcaaatgtc agagagagta atttctcctc    11100
atatgttgtt agactctata ttataaaaat ggggtgacag taatatattt gaacataaat    11160
aaactttcaa agtgagatat ctgcgccgat agaatgtgat tatttgccat gttgttcgaa    11220
tattcgcagt gtagagttat aagatatgag catattcatt agaatctaat gatggaaatt    11280
taagttagca cgtataggat atgtaggaac aagtctgtta aatttcaaat ataatgaaat    11340
aaaatagaag gactttatga atatgaatga caatgggcct aaagttagta tctatatatc    11400
tacttttaac aggctagaga aattaaaaag ggcgatagat tctgtttttg cacaagacta    11460
tcttaattgg gaattactaa tttgtgatga tgcatctacg gatggtactt ttgaattctc    11520
cagtgagtta gagttacgcg atgaaagagt tcgctatttc aggaatgagt ccaataaagg    11580
agcatgtgag acaaggaatt taggtatttt taatgcgaag ggtaaattta ttactggtct    11640
tgatgatgac gatgaattta ctccaaatag actttcagtt tttttaaaaa actgggatga    11700
tagatattct tttttgtgtt gcaattttaa aaataaatat ccaacaggaa aagaagaata    11760
ttactataaa ataaaaaaag agcgttgtat ttataattat aaagacatgc tttttgagaa    11820
tgaagcttca aatcagatat ttacattaac agaacgatta cagcaaatac atgggtttga    11880
taaaacagta aaacgtcttc aggattggga tacatggtta aggttgtctt ttagatatgg    11940
tgattttgta cgatataatg tttgtacata tattatgaat catgaccatc aacctagtga    12000
aataagagtg tcccagaatg aaaaaattgc tgactcactt ttatctttag ctaaaagaaa    12060
tagagggttg tattctaatg acgaatatag gtacatggaa tttatagtca actcaatgaa    12120
aggtaacatg ttttttttctg aaagtttata ttggacttat aagaagaaaa atccaaagtt    12180
tattgttaaa tattttttaa aaagataatc atatgactaa aattgatgtg ttactcgcaa    12240
cgtacaatgg tgagaaatat gttaaagagc aaatctcatc agttcttaat aattttgata    12300
agctaaaaaa ttcggaatgc acgatattaa tttcggatga tggttctaca gacagcaccg    12360
tggatataat taaacgtatg tccgaggaag acccaagggt tttgttttta gatggtaata    12420 aaaaggggg ggtaaaatat aattttaact acttaatcca acatacagat gcagattatg     12480 tgttttttg tgatcaagat gacttgtggt tgccaaataa aatgcacatc tttatggata    12540
gattcaacat cgaagaagtt aattttaatg gtcctatatt agtgcactcg gacttatgtg    12600
tagcagacat caatctttcg cctataaatg tgtcgatgtt tgattatcaa atgataaata    12660
```

```
aatctccgaa tctagcagaa ttattggtga gcaactctgt cactggatgt gtaatggcgt    12720
gtaataaaaa attaattgat ggaatcaaac tgtcgcagat ctctaagtcg ataatgcatg    12780
attggtatat tgcattatat gcatcgtcgt ttggcgttat ttcctttgtt gataaggcat    12840 taatactta tcggcagcat ggtgggaatc aagtgggggc taaatccttt tcactgaaag    12900
atgtacttaa gttttctggc ataaaagata aattagtgaa tgcgagaagg tctgttttaa    12960
atactagaga acaatcagct ttgtttattt ctgatttcgg tgataaatta agcatggaga    13020 aaagataat atttgaaagt tatataaatt cttttaatgg aggggtttta aataggatga    13080 atttatttt ttacaaaaga gtaagaaaaa ctagcttttt aagaaattta gtattctttt    13140
tgatttatgt gacaaagatt taaaatatta tctaatagta atatactata ggagaaaata    13200
agtgtttcat tcaaaatcgt gttcgagtat tggtgtgata tgttttttt taattattcc    13260 taattctgtt aagtctgctg aatttaatgc gttaggcaaa ccaacacaag ataacgttca    13320
aaatgaacag tctacctata gtaatagtat tttaagtggt agatacactt tcggcatgag    13380
aaaaaatgcg gttgtttctt catttgtagc taataatagt agcccactta atataccggt    13440
gttgggatta gggtctgtct ctggtttagc tcattattta gatagagatt cggttgcttt    13500
gtatgctgaa ataattcat caccatttag aaaatgggag aaaataaagt cgcccaagat    13560
cactcccacc tctgtgttat ctgaggatat aagtccaact aatatcaagg ttggtatgat    13620
cattgaaaca gagacacagc ccaagtggtc tacatatgta gtatcagtag tgcccggtaa    13680
aatcattacc gcagggtggg ttaacttaaa aactaaacgt atgggtactc cagataatca    13740
ttcatcctta gttattaatc ctgttacaaa aatatggagt gctaatttta atttgatttt    13800
ccctgacggg gggcgagcca caaaggtgt tgtacaagaa aatggaatta ttaataattc    13860
ggcgactagt aaaaatgtta atggtgtcga tacggttgtt ttaccgcaat caaaatttga    13920
tggaaatata gcatatctcg cgcgctcaac atcgttaggt aatgcaaaaa atgggaata    13980 tggttttgta tcgataggta atagagtttc atttagtagt agagacaatc aaattaattc    14040
acctgatatt agtttctatg atgaatcaaa aagcaaaata ggcttacttt tttcagggca    14100
aaacacttcg cattctatag tatggaaaaa cggggatact atagttgctt cagtatcacc    14160
tcgaggtgaa attgaaaaat taaatttcaa aacaaagata ataaactctt cccaagcatt    14220
agattctaat tttggtcggt atattttaa aattaactca aatatagata ttactttacc    14280
ggatgaaaaa gatctaacag atggttatac tctaaaatta accagtataa atgataatga    14340
ttttattgtg tctgtgaaat caataaataa taagaagctc aatggtgttg agagtttaaa    14400
gctgaaacat ggccgctgga atcttgaggc tgttttatttt caaaatgaat ggataattga    14460
ataacactat aagttattcc ataaaatagg tgagattcat gccgttattt ttaactaaca    14520
ttacactttt tttgtatttt ttaatttcgc tatttctatt attgttatca gtagtaagta    14580
ttatttgcaa aagtaaaaaa cttgattta ttgttttcct tattattggg ataatgatgg    14640 tttgtttta tgggcttagg tttcctggaa actcagatac tagaatgtat ttacaaggat    14700
ttgattcttt atctagttta gatagcttta tgtggagttc tggtttctat gttttaatga    14760
aatctataaa aatcattaat aacagccatg atgcatatat tttcttaagt tccttatact    14820
ttgttttagc ttttatgtta gttggaattc tatattgtaa ggaccgatat tataagtctc    14880 ttttttttact aacatgtttt tatagctgga gtgtgttaga tttagcagtt aatacatata    14940
ggcagggaat agcaattcct tttataattc ttggggtcta ttttctgaat agcaagaaaa    15000
atatacttgc tgttgttgct atttctatag cattaacaat tcactggggg agttctgtaa    15060
```

```
tcgtagctct ctattttatt gctatttatt tatcgaagca tttaaggcta ttaaaaatag   15120 taacttttt tactcttatg ttgtttacct tatctttctt tataaacttt gaatttgcag   15180
gttctctttc taaaagttct cttattagtt cattacaagt tctctttgtt ggtgttgatt   15240
taacttcaaa aattgatgca tatttagggg gcggtgttgt tggggcaagg ttttatgata   15300
tgccgagtct tcaacgatta tattttttctg gggagattta tattgcaata ttaattttct   15360 cattttttt ccttaccaga aaagccaaag atcccataat tacatctggt aattttgtca   15420
tgatttattc cttttttact attgtggcgt tttatggtgt tgttttaatt tcaatgacat   15480
ggtttattcg taatttttac tgggctgttc ctattacacc tgttctatat gttctaatct   15540
tgcagtatta tgaaaagaa aacgtaaaaa aacatcattt tttattacta ctatttgtaa   15600
tatttcaaat agcattttct attgaaactt tttggcgagc tcctttgata gatttagtct   15660
atccttactg aatttattag aagttatgaa atttatttaa catgagtgat aataatgaag   15720 aatatttgc ttgtgatctt atacaataag cagatcgtag actcatccac tcttttatca   15780
ttggctaaaa gtgattataa aggtgatgtc gtaattttta ataatggacc tttacctgtt   15840
agtaatactt gtgcatctct tttagcgatg aaacgagaca atcaaatagt acgaattgaa   15900
gaggatttaa acaatagacc actcagtatt atttacaatg atttcttgga actcaatggt   15960
tatgataatt attttatttt tgatgatgat actgtcatac ccaatgattt tttcagtgct   16020
aaaatacgga ataattgcca gttgtcgcta ccacttattt tgtcagagaa aacaaatata   16080
atacattatc caaaaataaa tggtgaacct tgtaatattg acgttctttc agtacaggat   16140
attgatgatg ttatatcgat tggatcaggg cttatgattc accgttcttt gatagaaata   16200
tttaagaaaa atcaccagca attatttgat gaaaaattcg cattatacgg tgtagactat   16260
agcttgtttc gccgcatatc taaactcaag tctaatgatg tcaagataaa aattgacata   16320
tccggagtgt taaaacattc actttcgagc gaggaaaata gtatttcttc ttttagaact   16380
cgtgaacgct taattgactt gattttgaac aaaattgtatt attctgaaca tgggagattg   16440 tataatttc tttccatagg caaaacaata atagagcaaa ttttgtctat gaatatttat   16500 agtgttttg tggttattcg agtcctttac catggtcagc atcccagaat acgtcaattc   16560
aaaaaataga cttacgtat attttttatt tctactattt tattgatatt ctactttata   16620
tattttgctt ttaagagagc gctgaaatga taactattaa taaaatagtt aaaaacaatg   16680
ctgttattaa tatcatttgg ttgtctgcag atagtctaat tagaatggga ttaggctttc   16740
ttgtatcagt atggcttgca cgatatctag daccgcatga atttggtatt tataattatt   16800
gtttggcgat tatcacaata tatgtttctg tagcttcttt aggaatgaac ggtgtagttg   16860
tcagagaggt cattaaaaac gaaaataaag ttaaagtgat catggggact tcgttgtacc   16920
ttcagatctt gggaagtctt ttagccagtg tcttagttac aattacaata tatgtactcc   16980
gcccgaatga ctgggggggta ttatttgctg ttttagtgat gttaccttca gtattactta   17040
gaagtagtga tattttttaag tattggttcg agtcaaaaat aaaatcgaaa tacactgttt   17100
tatcacaaaa tattgctttc tttataagct cagctgttaa aatatcaata atttatttta   17160
aggggtcata cttatatgtc tgtgcaactg tttctttaga ggcactgatc acttgtttgc   17220
tcctttactt ttattataaa aagaatcatt catccgaaga gaaatggcta tttgattatt   17280
atgaagctaa aagattatta tctttaagtt ggcctttaat attatcgggt gtcgctttta   17340
tgttatacat gcgaattgac caaataatga ttgggaatat gattggtgat tctgcagttg   17400
gtatttactc tgttgctgtg aaaatggttg aggtttggta ttttttccca gttgcaattg   17460
```

```
tcagttcttt atttccaaag ataattaagc ttagagaggt taatgtcttg gaatataata    17520
aacggttaca gttttatat gatattttag tcgttcttag cgtttcaatt gctttgattg     17580
tgacatttct ttctgattat attattgggt ttttctatac tcatcaatat actgaagctt    17640
caattctaat aaaaatatat gcgtgggtta gtgtcttta tttttaagt tctgctagtg      17700 gtcgttggta cataaacgaa ggattacaaa aatatgcact aatagaaat ttaattggtt     17760 tggttatggg ggttgttta aatttcttat taatcccgaa atatggttca ttaggttctg     17820
tttatgcaac gttgattgcc tatgcatgtg ctggatattt atttgatatt ttgtcaaaaa    17880
aaacaagagt tgccttttat caaaaaacga aggcattatg gattccaggg gctttaatcc    17940
ggttagttaa gaattttagg tgaaaaaatg aatgataaag taatccttta cggcgcatat    18000
gatcgttata attatggtga taatttaatg ccgatcttgt tagaaagatt cctgaagatt    18060
aattttccgg ataaaactag gaccattgac tttatttatg cgtcaatcga ttcttctgat    18120
ctaagtaaat ataagtgtta ttcttcaata gctatgaaaa atctgcttta tactcaacat    18180
aattcatcaa ttatagttgt aggaggcgag gtattaggag cagatgttgg aacgttgtat    18240
acacatgtac aacaaagcca attttatact cgaattttaa aaaaaataag aaggtttcaa    18300
ccaaaactat tgtcaactat tgctaaaatg ttctaccctg cggtttggga ttatccatac    18360
atacctcaaa aagcaagttt taagaataat gtcaaggtaa tatacaatac tgttggtgga    18420
gttcctgttt cttcacaaac taaatatatc gctcaagcgg aatatatatc tgcaagagat    18480
cgacgtacat atgaagaggt aacaaagtgg gccagtgcag agttagttcc agattctgtt    18540
cttatcgcat caaaaattat tgatgatcag ttcatgcaag attttgtccg caagaaaata    18600
attgattatt gtgcaacaaa taagtttatt acagtgcagg cctgccctta taagttaat    18660 ttttctgctc aagatcttgc atatcaatta gataatgtaa atcccaatc aagtatagat     18720 gtagttttac ttcctattgg ttacgcaagt ggtcatgatg atgtaatctt tcttcgagaa    18780
gtacaaaaac tggctaaaac tgagcttaag cttgagtacg aattaaatat ttgggaaata    18840
atgtattttc tttctcactc tcattcattc tacggtacta gtttgcatgg aattattaca    18900
gcaatgtcgt ttggtgtacc acattttgt attgatgaac gaatagaaaa aataaaatca    18960
ttcgttcaga catggagtgt tggacccttt actcaaccta taagcatttt tgatataaaa    19020
gatagtgtta gtaaaatgaa tgactatgat aattctgatt tattaaagtc ggtggagtat    19080
gcccagcaga tcatatctga aagtttgaaa aagattccc atatttgta atgtattaaa     19140 ttatttataa aatattatgt tttgttgtag gtggtttat tttaacctt aactctttca     19200 acttttatgc taggcggatt ccgttctttg agctaacata atcatcacat ttaagctgcg    19260
agtttgtcgc agtgaccacc ccagacagga gtaagtaatg tccaagcaac agatcggggt    19320
tgtcggtatg gccgtgatgg ggggtaacct tgcgctgaac atcgaaagcc gtggttatac    19380
cgtctccgtt ttcaaccgct cccgtgaaaa gaccgaagaa gtgattgccg agaatccagg    19440
caagaaactg gtcccttact atacagtaaa agagtttgtt gaatccctcg gaacaccacg    19500
tcgtatcctg ctgatggtga aggcaggggc tggtaccgat agcgccatcg attccctgaa    19560
gccttacctc gataaaggcg acatcatcat tgatggcggc aacaccttct tccaggacac    19620
catccgtcgt aaccgtgaac tgtctgccga aggttttaac tttatcggta ccggtgtttc    19680
cggtggtgaa gaggggggctc tgaaagggcc ttccatcatg cctggtggcc agaaagaagc    19740
ctatgagctg gttgctccga ttctgaagca gatcgcggca gttgctgaag acggtgagcc    19800
gtgtgttacc tatatcggtg ctgatggcgc tggccattat gtgaagatgg ttcataacgg    19860
```

```
catcgagtat ggtgacatgc agctgattgc cgaagcttat gcgctgctga aaggtggtct    19920
gacgctctct aatgaagagt tggcgcaaac cttcactgaa tggaacgaag gcgagctgag    19980
cagctacctg atcgacatta ccaaagatat cttcaccaag aaggatgaag agggtaaata    20040
cctcgttgat gttattcttg atgaagccgc aaacaaaggt accggcaagt ggaccagcca    20100
aagctcactg gatctcggcg aacctctgtc tctgatcacc gagtccgtgt ttgctcgcta    20160
tatctcttcg cttaaagacc agcgtgtagc cgcgtcgaaa gtgctgagtg gtccgcaggc    20220
tctaccggcc ggtgataaag cggaatttat cgaaaaagtt cgtcgcgcgt tgtacctcgg    20280
taaaatcgtt tcctatgctc agggcttctc tcaactgcgt gctgcttctg atgaatacaa    20340
ctgggatctg aactacggcg agatcgctaa gattttccgc gctggctgca tcattcgtgc    20400
gcagttcctg caaaagatca ctgatgctta tgcgcaaaac gctggcattg ctaacctctt    20460
gctggcgccg tacttcaaac agatcgctga tgactatcag caagcgctgc gtgatgtcgt    20520
ggcttatgcc gtgcagaatg gtattccggt accgacgttc tctgccgcaa ttgcctacta    20580
cgacagctac cgttccgcag ttctgccggc taacctgatc caggctcagc gtgattactt    20640
tggtgcgcac acctataagc gtactgataa ggaaggcgtt ttccatactg agtggttaga    20700
gtaa                                                                 20704
```

US 8,110,359 B2

PCR METHOD FOR IDENTIFIYING A SEROTYPE OF *KLEBSIELLA PNEUMONIAE* BY USING CPS REGION PRIMERS AND APPLICATION THEREOF

BACKGROUND OF THE INVENTION

1. Field of the Invention

The present invention relates to a method of identifying a serotype of *Klebsiella pneumoniae*, in particular to a method using specific polymerase chain reaction (PCR) primer sets designed according to a fragment of a capsular polysaccharide synthesis (cps) region to identify a K57 or a NTUH-N1 serotype.

2. Background of the Invention

*Klebsiella pneumoniae* belongs to the family of Enterobacteriaceae; which is a Gram-negative, facultative anaerobic, rod shaped bacterium with polysaccharide capsules. It's an opportunistic infectious pathogen. Strains of *Klebsiella pneumoniae* exist in the respiratory or digestive tract of healthy people. Infection occurs most commonly in people with low immunity that usually causes serious infection, and may result in pneumonia, septicemia, urinary tract infections, or wound infections and the like.

Pyogenic liver abscess caused by *Klebsiella pneumoniae*, which was always combined with septicemia, was found with unique clinical characteristics over the past two decades. This is a global emerging disease, particularly common in Taiwan. Different from the traditional disease caused by *Klebsiella pneumoniae*, people acquired this disease led an active daily life prior to hospitalization. Most patients do not have intra-abdominal infections or biliary tract diseases but may have peritonitis or septic shock, or may further be combined with bacteremia, septic endophthalmitis, meningitis, and so on.

The known virulence factors of *Klebsiella pneumoniae* include capsular polysaccharides, lipopolysaccharide, adhesions, membrane and extracellular protein. Among them, capsular polysaccharides are the major virulence factor and the base for serotype classification. There are at least 77 serotypes for *Klebsiella pneumoniae* according to serum epidemiology. The virulence of each strain varied with serotype. For example, serotype K1 or K2 has higher severity of infection (more virulent) than others, which cause pyogenic liver abscess easily, followed by combination with meningitis and endophthalmitis. The identification of serotypes was carried out by immune response using the immune sera (antibodies) to react with the extracted capsules of *Klebsiella pneumoniae* from the patients to determine the precipitation line with the reference strains of all serotypes. However, drawbacks of this method include low specificity, low sensitivity, and high expenses of serum.

Pyogenic liver abscess induced by infection of *Klebsiella pneumoniae* is susceptible to first generation antibiotics cephalosporin and gentamicin. However, mortality as high as 10-20% for primary liver abscess and as high as 30-40% among those with meningitis has been reported with effective doses of antibiotics. Due to the serious and invasive *Klebsiella pneumoniae* disease in epidemiology, it is important to develop a *Klebsiella pneumoniae* serotype detection method to facilitate the early diagnosis and rapid treatment in order to lower the mortality and provide insight to the prevention and treatment of diseases associated with *Klebsiella pneumoniae*.

SUMMARY OF THE INVENTION

The objective of the present invention is to provide a method of identifying a serotype of *Klebsiella pneumoniae* using specific PCR primer sets. The primer sets are designed according to the sequence of capsular polysaccharide synthesis (cps) region. The method comprises: (1) extracting DNA from a sample of *Klebsiella pneumoniae* for use as a DNA template; (2) performing PCR using the DNA template from Step (1), and primer sets of PCR primers comprising a primer set of nucleotide sequence #8282-#19243 of SEQ ID NO:44 and a primer set of nucleotide sequence #6039-#19131 of SEQ ID NO:45; and (3) identifying a K57 serotype of *Klebsiella pneumoniae* if PCR products are found from the primer set of SEQ ID NO:44, or identifying a NTUH-N1 serotype of *Klebsiella pneumoniae* if PCR products are found from the primer set of SEQ ID NO:45.

Another objective of the present invention is to provide a method of identifying a serotype of *Klebsiella pneumoniae* based on immune response. The method comprises: (1) obtaining capsular extracts from a sample of *Klebsiella pneumoniae*; (2) reacting the capsular extract of Step (1) with anti-NTUH-N1 antiserum; and (3) identifying a NTUH-N1 serotype of *Klebsiella pneumoniae* if positive result is revealed.

Yet another objective of the present invention is to provide an isolated and biologically pure *Klebsiella pneumoniae* strain, comprising an identifiable characteristics of *Klebsiella pneumoniae* A1517 stored in Bioresource Collection and Research Center (Food Industry Research and Development Institute, Hsinchu, Taiwan) with an accession number of BCRC No. 910412 as well as the identifiable characteristics of serotype NTUH-N1. The strain can cause pyogenic liver abscess and septicemia, which contains the nucleotide sequence of SEQ ID NO:45 and can be used to prepare anti-NTUH-N1 antiserum.

Still yet another objective of the present invention is to provide a kit for detecting a serotype of *Klebsiella pneumoniae*, comprising a primer set of nucleotide sequence #8282-#19243 of SEQ ID NO:44 or a primer set of nucleotide sequence #6039-#19131 of SEQ ID NO:45.

Still yet another objective of the present invention is to provide an isolated gene of capsular polysaccharide synthesis (cps) from *Klebsiella pneumoniae*, comprising SEQ ID NO:44 or SEQ ID NO:45, and a complementary sequence of SEQ ID NO:44 or SEQ ID NO:45. The *Klebsiella pneumoniae* can cause pyogenic liver abscess and septicemia clinically. The isolated gene can be used in rapid molecular diagnosis to determine if the patients are infected by serotype K57 or NTUH-N1 of *Klebsiella pneumoniae*, and to have early diagnosis and treatment for decreasing the mortality.

These methods and the kit comprise the primer set of nucleotide sequence #8282-#19243 of SEQ ID NO:44 is selected from the group consisting of a first primer set (SEQ ID NO:21 and SEQ ID NO:22) and a second primer set (SEQ ID NO:23 and SEQ ID NO:24); while the primer set of nucleotide sequence #6039-#19131 of SEQ ID NO:45 is selected from the group consisting of a third primer set (SEQ ID NO:25 and SEQ ID NO:26), a forth primer set (SEQ ID NO:27 and SEQ ID NO:28), a fifth primer set (SEQ ID NO:29 and SEQ ID NO:30), a sixth primer set (SEQ ID NO:31 and SEQ ID NO:27), a seventh primer set (SEQ ID NO:32 and SEQ ID NO:33), and a eighth primer set (SEQ ID NO:34 and SEQ ID NO:35).

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
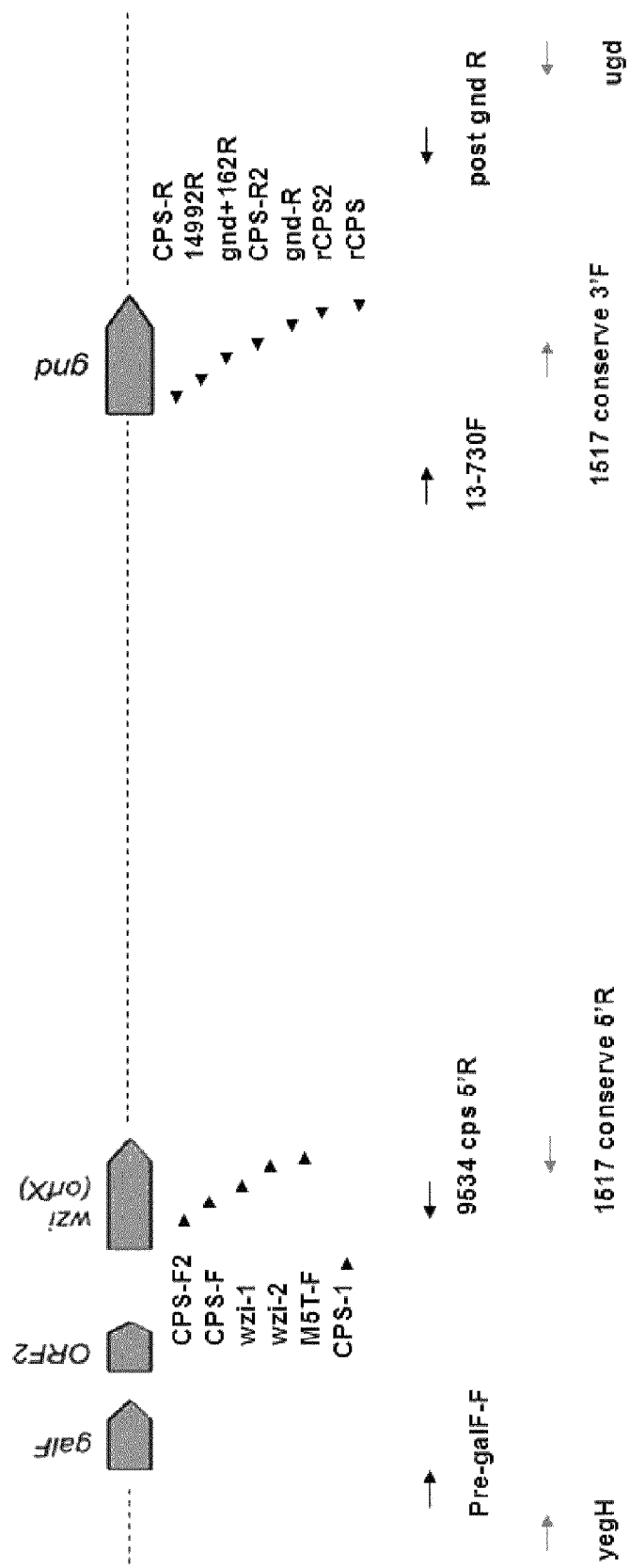
FIG. 1 Diagram of the capsular polysaccharide synthesis (cps) region and the primers used for PCR amplification of cps regions in the present invention.

The present invention used the strains listed in Table 1 to establish a method of identifying a serotype of Klebsiella pneumoniae in the field samples. Klebsiella pneumoniae strain A1517 was screened and isolated by the present invention, which was stored in Bioresource Collection and Research Center (Food Industry Research and Development Institute, Hsinchu, Taiwan) with an accession number of BCRC 910412 on Nov. 20, 2008. The nucleotide sequences of capsular polysaccharide synthesis (cps) region from A1142, A1517, and A7754 strains were determined. The specific primers were designed to identify a serotype of Klebsiella pneumoniae according to these sequences to perform PCR. Classic immune responses or other serotype detection method with high sensitivity were used to confirm the accuracy of the serotype detection method in the present invention. Strain A1517 was therefore identified to have a novel serotype NTUH-N1, and strain A1142 as well as strain A7754 were determined to belong to serotype K57.

Example 1

Establishment of Identification Method for a NTUH-N1 Serotype and a K57 Serotype of Klebsiella pneumoniae 1. Bacterial Strains and Preparation of Plasmids All the bacterial strains used in the present invention were listed in Table 1, which include forty-two clinical isolates of Klebsiella pneumoniae obtained from patients admitted to the National Taiwan University Hospital (NTUH) with pyogenic liver abscess with or without septic complications, such as meningitis and the cps genotypes of A1142, A7754, and A1517; twenty-one non-blood isolates from nonseptic patients at the NTUH; thirteen strains from patients at En Chu Kong Hospital (ECKH; Sansia, Taiwan); thirty four strains obtained from patients at Far Eastern Memorial Hospital (FEMH; Banciao, Taiwan); twenty four strains purchased from the American Type Culture Collection (ATCC), including strain MGH78578; eighty strains from Canada (Department of Medical Microbiology, University of Manitoba, Winnipeg, Manitoba, Canada); and one strain from Finland (Department of Clinical Microbiology, Kuopio University Hospital, Finland). Klebsiella pneumoniae and Escherichia coli were cultured in Luria-Bertani (LB) medium supplemented with appropriate antibiotics, including ampicillin (100 µg/ml) or kanamycin (50 µg/ml).

TABLE 1

Bacterial strains and plasmids used in the present invention

| Strain (collection number) or plasmids | Description or Genotype Reference or source |
|---|---|
| Bacterial strain | |
| Klebsiella pneumoniae strains | |
| NTUH-K2044 | Clinical isolate of K1 strain; isolated from a NTUH patient with septicemia, pyogenic liver abscess plus meningitis |
| A1142 | Clinical isolate; isolated from NTUH patients with septicemia and pyogenic liver abscess |
| A7754 | Clinical isolate; isolated from NTUH Diabetes Mellitus patients with septicemia and pyogenic liver abscess |
| A1517 | Clinical isolate; isolated from NTUH Diabetes Mellitus patients with septicemia and pyogenic liver abscess |
| NYUH (21) | Clinical isolates; isolated from a NTUH patient without septicemia (includes 0708) |
| ECKH (13) | Clinical isolate, isolated from ECKH patients (include strain E7, E12, E13) |
| FEMH (34) | Clinical isolate, isolated from FEMH patients |
| ATCC (24) | strains purchased from the American Type Culture Collection (including MGH78578) |
| Canada (80) | strains isolated from Canadian patients with septicemia (blood and cerebrospinal fluid) |
| Finland (1) | strains isolated from a Finland patient with pyogenic liver abscess |
| Escherichia coli | |
| DH10B | F⁻ mcrA Δ(mrr-hsdRMS-mcrBC) Φ80 lacZ ΔM15 lacX74 recA1 endA1 araD139 Δ(ara, leu)7697galU galK λ⁻ rpsL nupG |
| EPI300 | F⁻ mcrA Δ(mrr-hsdRMS-mcrBC) Φ80dlacZ ΔM15 lacX74 recA1 endA1 araD139 Δ(ara, leu)7697galU galK λ⁻ rpsL nupG trfA |

TABLE 1-continued

Bacterial strains and plasmids used in the present invention

Strain
(collection
number) or
plasmids        Description or Genotype Reference or source Plasmid pGEM-T Easy    pGEM-T Easy T-A cloning Promega
pGEM-T         pGEM-T Easy was inserted with Km (kanamycin)
Easy-Km        cassette from pUC4K into NdeI site for trans-
               complementation experiment
CopyControl    Long PCR product cloning
pCC1
pKO3-Km        pKO3-derived plasmid, with an insertion of Km
               resistance cassette from pUC4K into AccI site 2. Serum resistance test for strains A1142, A7754, and A1517

The serotypes of strains A1142, A7754, and A1517 isolated from patients were identified using serum resistance test. These bacterial strains were mixed with human sera from healthy volunteers. After incubation with serum for 3 h, the CFU counts in A1142, A7754, and A1517 decreased respectively to about 1%, 20%, and 4% of those in the initial inoculum. Therefore, the three strains were all serum sensitive and were less virulent than serotype K1 and serotype K2.

3. Nucleotide Sequencing of the cps Region

The nucleotide sequences of capsular polysaccharide synthesis (cps) region obtained from PCR amplification (FIG. 1) with the specific primers of *Klebsiella pneumoniae* were determined to compare the difference of cps sequences among various serotypes, to provide unique PCR primer sets for identifying serotype and to identify the genes needed for capsular synthesis.

Primers for conserved sequences flanking the cps region were designed according to the sequences of the cps genomic regions of *Klebsiella pneumoniae*. PCR amplifications were performed and the nucleotide sequences were determined (FIG. 1). Primer pairs of serotypes K1, K2, and K52 were designed as listed in Table 2 (SEQ ID NO:1~10). Cps regions from different serotypes (other than serotypes K1, K2, and K52) can also be amplified with various primer pairs. The PCR reaction contained: 1 μg template genomic DNA to a solution containing 5 μl of 10× buffer, 5 μl of 25 mM $MgCl_2$, 2.5 U of LA Taq polymerase, deoxynucleoside triphosphates at final concentrations of 0.5 mM each, and primers at final concentrations of 0.4 mM each in a total volume of 50 μl. The cycling program consisted of one denaturation step of 2 min at 94° C. and 10 initial cycles of 10 s at 98° C., 30 s at 63° C., and 12 min at 68° C., followed by 20 iterative cycles of 30 s at 98° C., 30 s at 63° C., and 12 min plus 20 s for each new cycle at 72° C. These amplified products were cloned into a CopyControl pCC1 vector, and the sequences were determined with primer pairs KAN-2 FP-1 and KAN-2 RP-1 (SEQ ID NO:11~12, sequence shown in Table 2) after in vitro transposition with an EZ-Tn5 KAN-2 insertion kit.

TABLE 2

Primers used in the present invention

| Primer name | Sequence ID (SEQ ID NOS.) | sequence | position | Purpose or reference |
|---|---|---|---|---|
| CPS-F | SEQ ID NO:1 | CGACCTGGCCTGGCTTTCCGATCG | wzi | cps region PCR |
| CPS-F2 | SEQ ID NO:2 | GCCGGGTTAGTGGTAAATGACAACG | wzi | cps region PCR |
| wzi-1 | SEQ ID NO:3 | TCATCCATCTGAGCCTGTCGAC | wzi | cps region PCR |
| wzi-2 | SEQ ID NO:4 | GAAGTTCTGGAACCAGTGGCTC | wzi | cps region PCR |
| M5T-F | SEQ ID NO:5 | TCATAACGGAGGATACCAGC | wzi | cps region PCR |
| CPS-R | SEQ ID NO:6 | CAAGCAACAGATCGGGGTTGTCGG | gnd | cps region PCR |
| CPS-R2 | SEQ ID NO:7 | CGAGGGATTCAACAAACTCT | gnd | cps region PCR |
| gnd-R | SEQ ID NO:8 | GATGGTGTCCTGGAAGAAGGTG | gnd | cps region PCR |
| 14992R | SEQ ID NO:9 | TACCGTCTCCGTTTTCAACC | gnd | cps region PCR |
| gnd+162R | SEQ ID NO:10 | GTAAGGAACCAGCTTCTTGC | gnd | cps region PCR |
| KAN-2 FP-1 | SEQ ID NO:11 | ACCTACAACAAAGCTCTCATCAACC | EZ-Tn5 KAN-2 Transposon | cps sequencing |
| KAN-2 RP-1 | SEQ ID NO:12 | GCAATGTAACATCAGAGATTTTGAG | EZ-Tn5 KAN-2 Transposon | cps sequencing |

TABLE 2-continued

Primers used in the present invention

| Primer name | Sequence ID (SEQ ID NOS.) | sequence | position | Purpose or reference |
|---|---|---|---|---|
| pre-galF-F | SEQ ID NO:13 | GAGCCGCTGAATAACCTGAA | upstream of galF | A1142 cps 5'PCR |
| 9534 cps 5'R | SEQ ID NO:14 | GCTCAGAAGAATAGGACGGT | wzi | A1142 cps 5'PCR |
| 13-730F | SEQ ID NO:15 | GTGCCATGGTGCTTGGTGG | A1142 ORF13'-ORF14' | A1142 cps 3'PCR |
| post gnd R | SEQ ID NO:16 | GATGACCATCGGTTCATGGA | manC | A1142 cps 3'PCR |
| yegH | SEQ ID NO:17 | GGCGCGACGTCATAATACTG | yegH | A1517 cps 5'PCR |
| 1517 conserve 5'R | SEQ ID NO:18 | GAGAAGGTAAAGCGGCCACC | wzi | A1517 cps 5'PCR |
| 1517 conserve 3'F | SEQ ID NO:19 | GACCGAAGAAGTGATTGCCG | gnd | A1517 cps 3'PCR |
| ugd | SEQ ID NO:20 | CGCGTTCGGGTTGATCTTTG | ugd | A1517 cps 3'PCR |
| 9471F | SEQ ID NO:21 | ATGGCGTGCCTCGTGAG | A1142 ORF10' | cps-PCR genotyping mutant construct |
| 9897R | SEQ ID NO:22 | GTTATAGCACCAATTACAGC | A1142 ORF10' | cps-PCR genotyping |
| 1142XF | SEQ ID NO:23 | GTCATCTGCACAGGATGACA | A1142 | cps-PCR genotyping |
| 1142XR | SEQ ID NO:24 | CTTCGCTACCGTGTAGCATT | A1142 ORF9' | cps-PCR genotyping |
| 1517XF | SEQ ID NO:25 | GCAAGACAAGAATGGGATGC | A1517 wbaP | cps-PCR genotyping |
| 1517XR | SEQ ID NO:26 | GACATACTACCGCATTTGCG | A1517 ORF8" | cps-PCR genotyping |
| 1517YF | SEQ ID NO:27 | CAGTGAGTTAGAGTTACCG | A1517 ORF9" | cps-PCR genotyping |
| 1517YR | SEQ ID NO:28 | GCTACACATAAGTCCGAGTG | A1517 ORF10" | cps-PCR genotyping |
| 12R STAR | SEQ ID NO:29 | GCAAGTGAGCAAAGTAATGC | A1517 wbaP | cps-PCR genotyping |
| 12 STAR | SEQ ID NO:30 | AGGCTCATCTCTCCCTTCAG | A1517 wbaP | cps-PCR genotyping |
| 15R-2 | SEQ ID NO:31 | GGGACACTCTTATTTCAC | A1517 ORF9" | cps-PCR genotyping |
| 7R STAR | SEQ ID NO:32 | CTGGGATGCTGACCATGG | A1517 ORF13" | cps-PCR genotyping |
| 7 STAR | SEQ ID NO:33 | CGTAGACTCATCCACTCTTT | A1517 ORF13" | cps-PCR genotyping |
| 3-2 | SEQ ID NO:34 | GAGGGTATTGATTTAGGTC | A1517 wzc | cps-PCR genotyping |
| 12R-2 | SEQ ID NO:35 | CTACAGAAACCATCCCGCC | A1517 wzc | cps-PCR genotyping |

TABLE 2-continued

Primers used in the present invention

| Primer name | Sequence ID (SEQ ID NOS.) | sequence | position | Purpose or reference |
|---|---|---|---|---|
| R5 | SEQ ID NO:36 | CTATTGAGCAGTCTGTAG | A1142 ORF12' | Mutant construct |
| 1142(9)5'R | SEQ ID NO:37 | TTTTAAGATAATCCTTATCGAG | upstream of A1142 wzy | Mutant construct (inverse PCR) |
| 1142(9)3'F | SEQ ID NO:38 | TCTTATTTGTGAGGTGTG | downstream of A1142 wzy | Mutant construct (inverse PCR) |
| K57-10394F | SEQ ID NO:39 | AGACTTTCTCGATAAGG | A1142 ORF10' | trans-complementation |
| 1142(10)5'R | SEQ ID NO:40 | TGCTTCTCTCATACACAC | upstream of A1142 ORF12' | trans complementation |
| CPS-1 | SEQ ID NO:41 | GCT GGT AGC TGT TAA GCC AGG GGC GGT AGC G | upstream of wzi | 4 |
| rCPS | SEQ ID NO:42 | TAT TCA TCA GAA GCA GCA CGC AGC TGG GAG AAG CC | gnd | 4 |
| rCPS2 | SEQ ID NO:43 | GCG CTC TGG CTG GTC CAT TTA CCG GTC CCT TTG | gnd | 4 |

PCR amplification was carried out with primers CPS-F and CPS-R2 (SEQ ID NO:1 & SEQ ID NO:2) for A1142 and A7754 bacterial strains. In addition, 5'-end of cps region was amplied with primers pre-galF-F and 9534 cps 5'R (SEQ ID NO:13 & SEQ ID NO:14), and 3'-end of cps region was amplied with primers 13-730F and post gnd R (SEQ ID NO:15 & SEQ ID NO:16) to get a complete cps region of A1142 and A7754 bacterial strains. The nucleotide sequence of the complete cps region of A1142 was listed in SEQ ID NO:44 with an accession number of AB334776 in GenBank database.

Another PCR amplification was carried out with primers wzi-2 and gnd-R (SEQ ID NO:4 & SEQ ID NO:8) for A1517 bacterial strain. In addition, 5'-end of cps region was amplied with primers yegH and 1517 conserve 5'R (SEQ ID NO:17 & SEQ ID NO:18), and 3'-end of cps region was amplied with primers 1517 conserve 3° F. and ugd (SEQ ID NO:19 & SEQ ID NO:20) to get a complete cps region of A1517 bacterial strain. The nucleotide sequence of the complete cps region of A1517 was listed in SEQ ID NO:45 with an accession number of AB334777 in GenBank database.

The PCR reaction contained the abovementioned reactants with the cycling program of: 96° C. for 3 min, followed by 30 temperature cycles of 96° C. for 30 s, 52° C. for 15 s, and 72° C. for 2 to 5 min. A final elongation step of 10 min at 72° C. was added. The sequence of PCR products were determined and combined with the sequence of the middle cps region to obtain a complete cps region of 10-20 kb DNA fragments (from galF to gnd).

Figure 2:
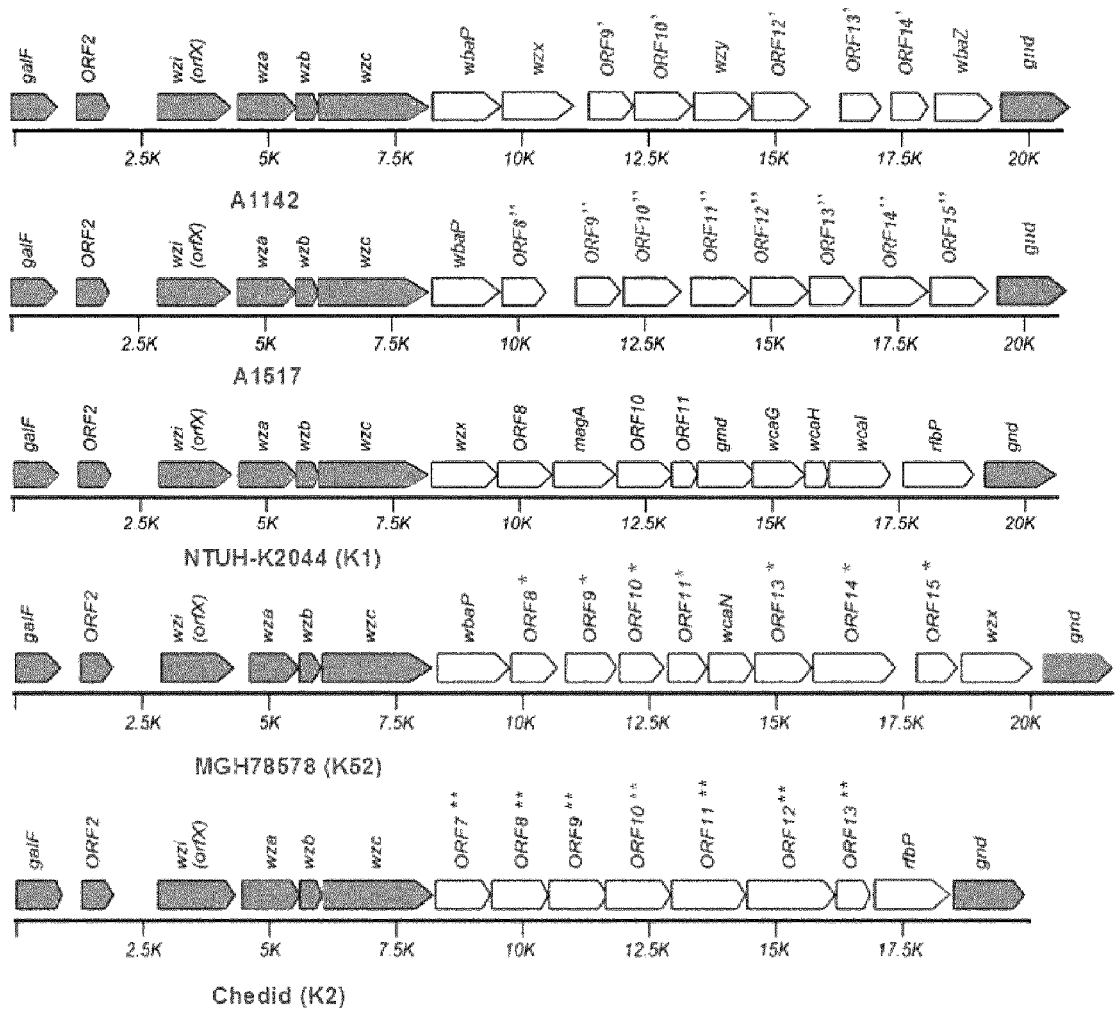
FIG. 2 Comparison of capsular polysaccharide synthesis (cps) regions between A1142, A1517, NTUH-K2044 (K1), MGH78578 (K52), and Chedid (K2). ORFs are shown by arrows. Black arrows indicate the ORFs conserved in these serotypes, and white arrows refer to the ORFs variable in these serotypes; ORFs with homologs are cited by putative gene names, and those without homologs are cited as numbered ORFs (ORF' in A1142, ORF" in A1517, ORF in NTUH-K2044, ORF* in MGH78578, and ORF** in Chedid); the axis below indicates position in kilobases.

Referring to FIG. 2, the genes of capsular polysaccharide synthesis (cps) regions of *Klebsiella pneumoniae* serotypes A1142, A1517, NTUH-K2044 (K1), MGH78578 (K52), and Chedid (2) were shown. Chedid is a lab strain, which is from Institute for Medical Science, University of Tokyo, Tokyo, Japan. ORFs are shown by arrows. Black arrows indicate the ORFs conserved in these serotypes, which are the cps sequence similar region, and white arrows refer to the ORFs variable in these serotypes, which are the cps variable region. The composition of the figure showed that cps region in different serotype had different gene structure. Therefore, serotypes A1142 and A1517 did not belong to any of the serotypes K1, K2, or K52.

On the other hand, sequence analysis of amplified 10-20 kb fragments of cps region of A1142 and A7754 with primer pairs CPS-F and CPS-R2 showed similar sequence. This indicated that both strains have the same serotype. In addition, the A1142 and a reference strain which belong to K57 have a very similar cps variable region (44 bases difference among 4323 bases), while A1517 has a quite unique sequence among any known serotype in cps region. It is suggested that this cps region in the present invention was responsible for capsular polysaccharide synthesis according to the figure and the predicted function of ORFs.

4. Serotyping of A1142, A7754 and A1517

K1 and K2 specific primers were used in PCR to detect the cps genotype of A1142, A7754 and A1517. Detection of serotype K1-K6 with *Klebsiella* antisera (SEIKEN) at the same time showed no result on these three strains. Therefore, they did not belong to serotype K1-K6.

Specific primer pairs were designed according to the nucleotide sequences of cps regions of these three strains since they did not belong to the major serotypes K1 or K2, the pyogenic liver abscess associated *Klebsiella pneumoniae* strains. PCR was performed by using reference strains with 77 known serotypes as templates. The PCR reaction contained: 1 µl template DNA to a solution containing 2 µl of 10× buffer, 2.5 U of Taq polymerase, 1 mM of each deoxynucleoside triphosphates (dNTPs), and primers at final concentrations of 0.4 mM each in a total volume of 20 µl. The cycling program consisted of one denaturation step of 3 min at 96° C. and 30 cycles of 30 s at 96° C., 30 s at 53° C., and 30 s at 72° C. Other serotype detection methods, as described below, were also used to confirm the PCR results.

(1) Identification of Serotypes A1142 and A7754

Figure 3:
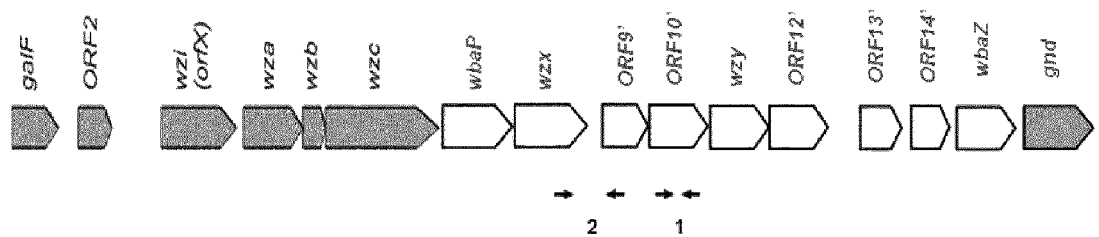
FIG. 3 cps PCR genotyping of strains A1142, A7754, and A1517. (A) Genetic alignment of the A1142 cps region and the primers for cps PCR genotyping. Primer pair 1, 9471F and 9897R; primer pair 2, 1142xF and 1142XR. (B) Genetic alignment of the A1517 cps region and the primers for cps PCR genotyping. Primer pair 1, 1517XF and 1517XR; primer pair 2, 1517YF and 1517YR; primer pair 3, 12R STAR and 12 STAR; primer pair 4, 1517YF and 15R-2; primer pair 5, 7R STAR and 7 STAR; primer pair 6, 3-2 and 12R-2.
Figure 3:
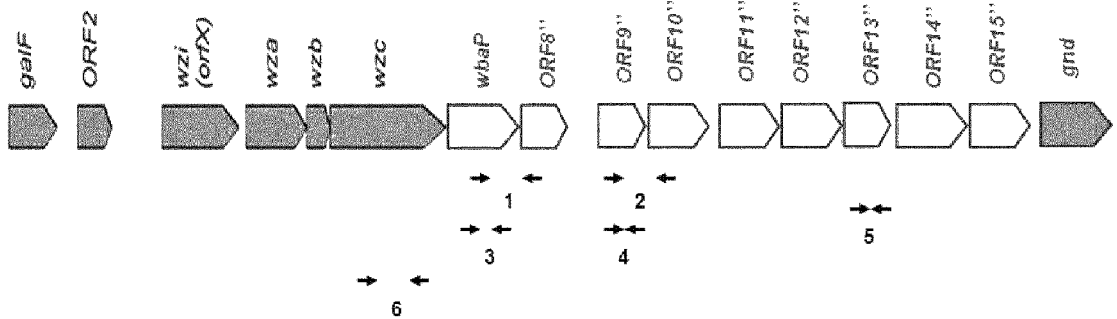

The designed specific primers for cps region of A1142 or A7754: a first primer set: 9471F and 9897R (SEQ ID NO:21 & SEQ ID NO:22), and a second primer set: 1142×F and 1142XR (SEQ ID NO:23 & SEQ ID NO:24) were used in cps PCR genotyping with the 77 known serotypes. The annealing sites for these two primer pairs are shown in FIG. 3. On the other hand, other primer pairs, which can be annealed to the cps region of A1142 or A7754 and showed sensitivity and specificity to serotype K57, were also applied in PCR genotyping. For example, primers designed according to nucleotide sequence of #8282-#19243 bases on SEQ ID NO:44 of the cps region of A1142. PCR products were only found with the primer pairs of 9471F and 9897R, as well as 1142×F and 1142XR against serotype K57. The data indicated that A1142 and A7754 belonged to cps genotype K57 and that the primers were specific for K57 cps PCR genotyping.

Further PCR screening was performed with primers 9471F and 9897R among total of 173 strains, which contained 21 NTUH nonblood isolates, 13 ECKH strains, 34 FEMH strains, 24 ATCC strains, 80 Canada strains, and 1 Finland strain. Only 2 of the 13 ECKH strains (designated E7 and E12) and the Finland strain have positive results.

Figure 4:
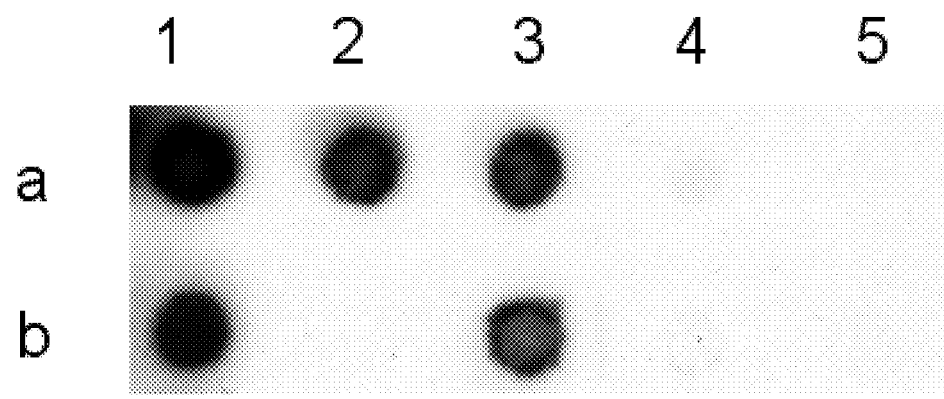
FIG. 4 Immunoblot serotyping of Klebsiella pneumoniae serotype K57. Anti-K57 antiserum was used as the first antibody and goat anti-rabbit IgG-HRP as the second antibody. (A) 1a, capsular extract of the K57 reference strain; 2a, A1142; 3a, A7754; 4a, NTUH-2044 (K1); 5a, MGH78578 (K52); 1b, A1142; 2b, wzy mutant of A1142; 3b, wzy mutant of A1142 with wzy trans-complementation. (B) 1a, capsular extract of the K57 reference strain; 2a, E7; 3a, E12; 4a, Finland strain; 1b, ATCC 35597; 2b, 0708; 3b, E13; 4b, YD20.
Figure 4:
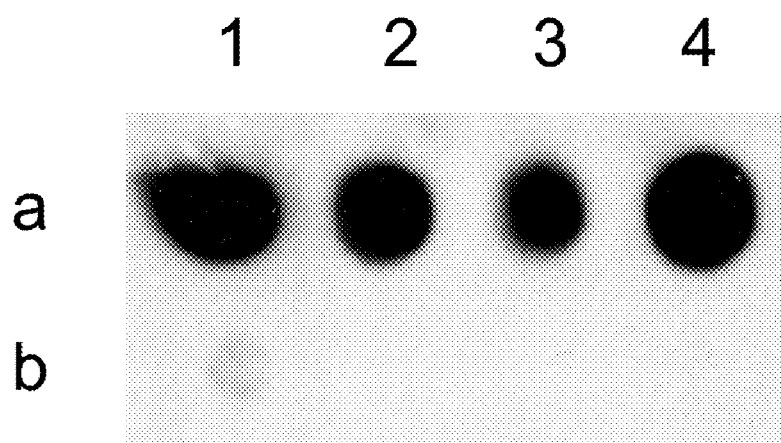

Immunoblot serotyping was further performed to confirm that A1142 belonged to cps genotype K57 in the present invention. Ten microliters of each capsular extract was vacuum spotted onto a nitrocellulose membrane. The membrane was blotted and blocked, followed by hybridization with K57 serotype-specific antiserum. The results are shown in FIG. 4. Compared to what was found for the K57 reference strain, capsular extracts of A1142 showed strong and clear positive results while the negative group, NTUH-K2044 of the serotype K1 and MGH78578 of the serotype K52, showed negative results. Immunoblot serotyping was also performed by use of other PCR-positive strains, the E7, E12, and Finland strains, and four of the PCR-negative strains (randomly selected), ATCC 35597, 0708 (NTUH nonblood isolate), E13 (ECKH strain), and YD20 (FEMH strain). The E7, E12, and Finland strains showed positive signals compared to the negative results revealed in other strains.

Figure 5:
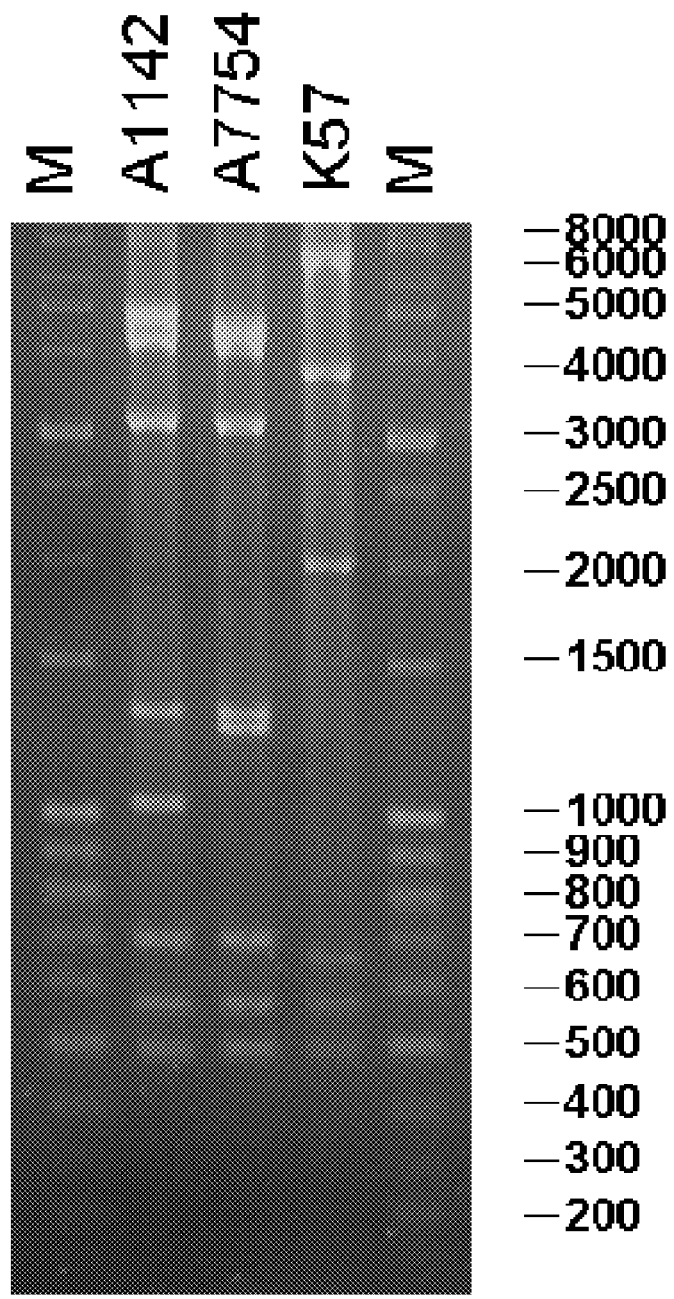
FIG. 5 cps PCR-RFLP analysis of the Klebsiella pneumoniae serotypes A1142 and A7754.

The cps PCR-restriction fragment length polymorphism (RFLP) method was carried out in the K57 reference strain, A1142, and A7754. PCR amplifications were amplified with primers wzi2 and rCPS2 (SEQ ID NO:4 & SEQ ID NO:43). The amplified products were digested with HincII, followed by electrophoresis (FIG. 5). The pattern of HincII digested fragments of K57 was quite different from that of A1142 or A7754 though both strains belonged to serotype K57. On the other hand, those of A1142 and A7754 were similar to each other, indicates a very similar cps region of both strains.

(2) Identification of Serotypes A1517

Six sets of primers, including a third primer set: 1517×F and 1517XR (SEQ ID NO:25 & SEQ ID NO:26), a forth primer set: 1517YF and 1517YR (SEQ ID NO:27 & SEQ ID NO:28), a fifth primer set: 12R STAR and 12 STAR (SEQ ID NO:29 & SEQ ID NO:30), a sixth primer set: 1517YF and 15R-2 (SEQ ID NO:31 & SEQ ID NO:27), a seventh primer set: 7R STAR and 7 STAR (SEQ ID NO:32 & SEQ ID NO:33), and a eighth primer set: 3-2 and 12R-2 (SEQ ID NO:34 & SEQ ID NO:35) were used in A1517 cps PCR genotyping. The annealing sites were shown in FIG. 3B. The eighth primer set can be used as specific genotyping primers for strain A1517 since the sequence of this region was different from other strains though it was located at the conserved cps ORF. On the other hand, primer sets other than these six primer sets, which can be annealed to the cps region of A1517 and showed sensitivity and specificity to serotype NTUH-N1, were also applied in PCR genotyping. For example, primers designed according to nucleotide sequence of #6039-#19131 bases on SEQ ID NO:45 of the cps region of A1517. Unexpectedly, no PCR products were found with the abovementioned primer sets among the 77 serotypes reference strains. The data indicated that A1517 did not belong to the 77 serotypes.

Further PCR screening was performed with primers 12R STAR and 12 STAR among the abovementioned 173 strains. Only one of the Canada strains (designated Canada 05-14) showed a positive result, which suggested that they belonged to same cps genotype of A1517.

Figure 6:
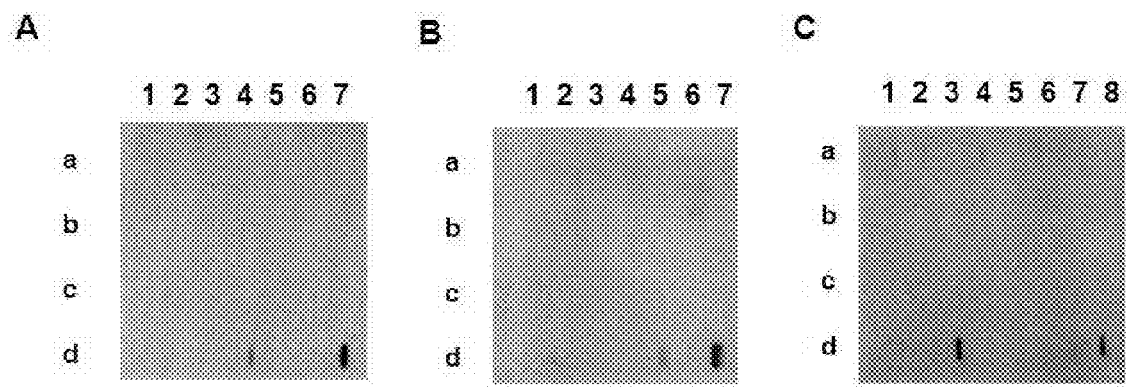
FIG. 6 Immunoblot serotyping of Klebsiella pneumoniae A1517. Anti-A1517 antiserum was used as the first antibody and goat anti-rabbit IgG-HRP as the second antibody. (A) 1a to 7a, K1 to K7; 1b to 7b, K8 to K14; 1c to 7c, K15 to K21; 1d to 6d, K22 to K27; 7d, A1517. (B) 1a to 7a, K28 to K34; 1b to 7b, K35 to K41; 1c to 7c, K42 to K48; 1d to 6d, K49 to K54; 7d, A1517. (C) 1a to 7a, K55 to K61; 1b to 7b, K62 to K68; 1c to 4c, K69 to K72; 5c, K74; 6c and 7c, K79 and K80; 1d and 2d, K81 and K82; 3d, A1517; 8d, Canada 05-14.

Immunoblot serotyping was further performed to confirm the result of A1517 serotyping in the present invention (with the abovementioned procedures, except the hybridization antiserum was replaced with anti-A1517 antiserum). The results are shown in FIG. 6 Serotypes K25, K53, K55, K56, and K58 had weak reactions with anti-A1517 antiserum (FIG. 6A, 4d; FIG. 6B, 5d; and FIG. 6C, 1a, 2a, and 4a, respectively), and Canada 05-14, which was considered to be of the same cps genotype as A1517, showed a strong positive result with anti-A1517 antiserum (FIG. 6C, 8d). Therefore, A1517 belongs to a novel serotype but not any of the 77 documented serotypes according to both the cps genotype and the capsular serotype observation.

Figure 7:
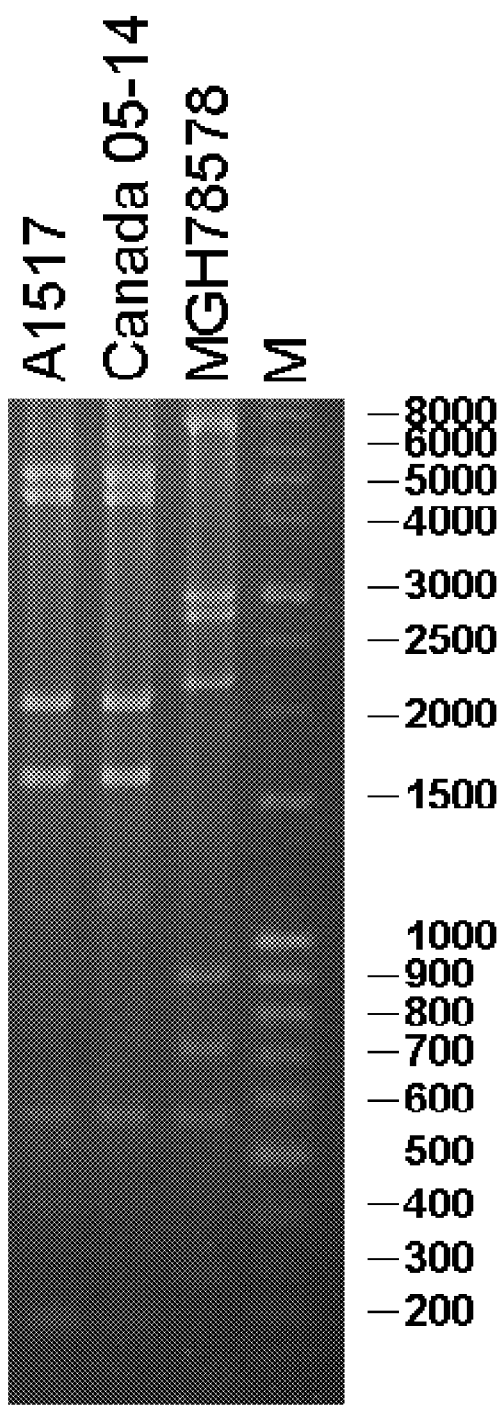
FIG. 7 cps PCR-RFLP analysis of the Klebsiella pneumoniae serotype A1517.

The cps PCR-restriction fragment length polymorphism (RFLP) method was also carried out in the A1517 and Canada 05-14 strains. PCR amplifications were amplified with primers CPS-1 and rCPS. The amplified products were digested with HincII, followed by electrophoresis (FIG. 7). The patterns of HincII digested fragments of A1517 and Canada 05-14 strains were very undistinguishable, while they were quite different from that of K52. On the other hand, sequences of the cps variable region of A1517 were very similar to those of Canada 05-14 (only 1-nucleotide difference in 2,479 bp), but very different from those of K25, K53, K55, K56, and K58 (<10% nucleotide similarity). These results indicated that A1517 belonged to a novel genotype but not the existing 77 reference strains.

Example 2

Effects of the wzy Gene to Serotype K57

To characterize the K57 determinant gene of the cps region in A 1142, an unmarked deletion mutant of the wzy gene located in the cps variable region of A1142 (K57) was generated in the present invention. The function of the wzy gene was studied, which was associated with capsule synthesis using a string test. A cps deletion strain of A1142 was generated by using a pKO3-Km plasmid constructed in the invention. First, primers 9471F (952 bp upstream of wzy, SEQ ID NO:21) and R5 (824 bp downstream of wzy, SEQ ID NO:36) were designed to amplify the target gene wzy and its flanking region. The amplified products were cloned to a pGEM-T Easy vector, followed by inverse PCR to delete the entire wzy gene with the intact flanking regions remained. The flanking regions of wzy were digested by restriction enzymes and ligated into pKO3-Km vector. Plasmid pKO3-Km_wzy was transformed into A1142, and a wzy gene deleted strain was generated after serial selection. For trans-Complementation test, the intact wzy gene and its ribosomal binding site were cloned to a modified pGEM-T Easy vector, which was transformed into the wzy mutant of A1142.

The result showed that the wzy mutant of A1142 lost mucoviscosity with a string test, indicating attenuated capsule synthesis. This mutant strain also showed negative results after immunoblot serotyping with anti-K57 antiserum. In transcomplementation test, the positive result was restored after transformation of a wzy-carrying pGEM-T Easy-Km vector into the mutant strain. Therefore, wzy was the essential gene for capsular synthesis of serotype K57. And the gene cluster of the cps region was responsible for the capsular synthesis.

Countercurrent immunoelectrophoresis and double immunodiffusion are commonly used for identifying the serotypes of Klebsiella pneumoniae. However, these two methods had problems in correct serotyping. Initially, double immunodiffusion was used to confirm if the serotype of A1142 belonged to K57. Sample to be assayed formed an ambiguous precipitation line in contrast to that for the K57 reference strain. Modified immunoblot serotyping method presently employed showed an increased sensitivity and reduced the consumption of antiserum. The result of immunoblot analysis with anti-A1517 antiserum also showed several cross-reactions. DNA sequences were different among A1517 and these known serotypes. Therefore, cps PCR genotyping would be a more sensitive and specific way for serotype identification.

On the other hand, a molecular serotyping method such as cps PCR-RFLP analysis, has a higher discriminatory power than classical serotyping according to recent studies. However, cps PCR-RFLP pattern variations were found among strains of serotype K57. This was also shown in the abovementioned example. The cps PCR-RFLP pattern of reference strain K57 was quite different from those of A1142 and A7754 though sequences of these strains in the cps variable region were very similar (FIG. 5). The serotype identification of Klebsiella pneumoniae is therefore very complicated.

From the description and results of the abovementioned examples, the present invention provided a more sensitive and specific method for serotyping, a PCR-based cps genotyping for capsular type, to solve the problems of insufficient specificity and sensitivity in conventional immune method. This PCR-based cps genotyping method not only solves the problems of insufficient specificity and sensitivity caused by conventional immune method, but can be applied in clinical diagnosis with the advantages of rapidity and low cost. In addition, the rate of unidentifiable strains can also be reduced by this method.

What is claimed is:

1. A method of identifying a serotype of *Klebsiella pneumoniae*, the method comprising:
   (1) extracting DNA from a sample of *Klebsiella pneumoniae* for use as a DNA template;
   (2) performing polymerase chain reaction (PCR) using the DNA template obtained from Step (1), and pair sets of PCR primers comprising a primer set selected from the group consisting of a first primer set, a second primer set, a third primer set, a fourth primer set, a fifth primer set, a sixth primer set, a seventh primer set and a eighth primer set; and
   (3) identifying a K57 serotype of *Klebsiella pneumoniae* if PCR products are found from the first or the second primer sets, or identifying a NTUH-N1 serotype of *Klebsiella pneumoniae* if PCR products are found from the third, the fourth, the fifth, the sixth, the seventh or the eighth primer set;
      wherein the first primer set is consisting of SEQ ID NO:21 and SEQ ID NO:22, the second primer set is consisting of SEQ ID NO:23 and SEQ ID NO:24, the third primer set is consisting of SEQ ID NO:25 and SEQ ID NO:26, the fourth primer set is consisting of SEQ ID NO:27 and SEQ ID NO:28, the fifth primer set is consisting of SEQ ID NO:29 and SEQ ID NO:30, the sixth primer set is consisting of SEQ ID NO:31 and SEQ ID NO:27, the seventh primer set is consisting of SEQ ID NO:32 and SEQ ID NO:33, and the eighth primer set is consisting of SEQ ID NO:34 and SEQ ID NO:35.

2. The method as claimed in claim 1, wherein a *Klebsiella pneumoniae* A1517 (BCRC No. 910412) is identified with the method of claim 1 as the NTUH-N1 serotype.

3. A primer set of identifying a NTUH-N1 serotype of *Klebsiella pneumoniae* comprising DNA of a NTUH-N1 serotype of *Klebsiella pneumoniae* for use as a template to obtain to a fragment of a capsular polysaccharide synthesis (cps) region of the NTUH-N1 serotype of *Klebsiella pneumoniae* through PCR, wherein the primer set is selected from the group consisting of a third primer set, a fourth primer set, a fifth primer set, a sixth primer set, a seventh primer set and a eighth primer set, wherein the third primer set is consisting of SEQ ID NO:25 and SEQ ID NO:26, the fourth primer set is consisting of SEQ ID NO:27 and SEQ ID NO:28, the fifth primer set is consisting of SEQ ID NO:29 and SEQ ID NO:30, the sixth primer set is consisting of SEQ ID NO:31 and SEQ ID NO:27, the seventh primer set is consisting of SEQ ID NO:32 and SEQ ID NO:33, and the eighth primer set is consisting of SEQ ID NO:34 and SEQ ID NO:35.

* * * * *